(12) United States Patent
Holz

(10) Patent No.: US 10,767,982 B2
(45) Date of Patent: Sep. 8, 2020

(54) SYSTEMS AND METHODS OF LOCATING A CONTROL OBJECT APPENDAGE IN THREE DIMENSIONAL (3D) SPACE

(71) Applicant: Ultrahaptics IP Two Limited, Bristol OT (GB)

(72) Inventor: David S. Holz, San Francisco, CA (US)

(73) Assignee: Ultrahaptics IP Two Limited, Bristol (GB)

( * ) Notice: Subject to any disclaimer, the term of this patent is extended or adjusted under 35 U.S.C. 154(b) by 97 days.

(21) Appl. No.: 15/953,320

(22) Filed: Apr. 13, 2018

(65) Prior Publication Data

US 2019/0017813 A1 Jan. 17, 2019

Related U.S. Application Data

(63) Continuation of application No. 14/723,370, filed on May 27, 2015, now Pat. No. 9,945,660, which is a
(Continued)

(51) Int. Cl.
*G06K 9/00* (2006.01)
*G01B 11/24* (2006.01)
(Continued)

(52) U.S. Cl.
CPC ...... *G01B 11/2433* (2013.01); *G06K 9/00201* (2013.01); *G06K 9/00355* (2013.01);
(Continued)

(58) Field of Classification Search
CPC ...... G06F 3/017; G06F 3/011; G06F 3/04815; G06F 3/04845; G06F 3/0416;
(Continued)

(56) References Cited

U.S. PATENT DOCUMENTS 2,665,041 A 1/1954 Maffucci
4,175,862 A 11/1979 DiMatteo et al.
(Continued)

FOREIGN PATENT DOCUMENTS

CN 1984236 A 6/2007
CN 201332447 Y 10/2009
(Continued)

OTHER PUBLICATIONS

Sundaresan et al., Markerless Motion Capture using Multiple Cameras, Computer Vision for Interactive and Intelligent Environment, Nov. 17-18, 2005 [retrieved Dec. 17, 2019], 12 pages. Retrieved: https://ieeexplore.ieee.org/abstract/document/1623766 (Year: 2005).*
(Continued)

*Primary Examiner* — Andrew M Moyer
*Assistant Examiner* — Dennis Rosario
(74) *Attorney, Agent, or Firm* — Haynes Beffel & Wolfeld, LLP; Ernest J. Beffel, Jr.; Paul A. Durdik

(57) ABSTRACT

Methods and systems for capturing motion and/or determining the shapes and positions of one or more objects in 3D space utilize cross-sections thereof. In various embodiments, images of the cross-sections are captured using a camera based on reflections therefrom or shadows cast thereby.

16 Claims, 35 Drawing Sheets

Related U.S. Application Data continuation of application No. 13/724,357, filed on Dec. 21, 2012, now Pat. No. 9,070,019, which is a continuation-in-part of application No. 13/414,485, filed on Mar. 7, 2012, now abandoned.

(60) Provisional application No. 61/587,554, filed on Jan. 17, 2012, provisional application No. 61/724,091, filed on Nov. 8, 2012.

(51) Int. Cl.

| | | |
|---|---|---|
| *G06T 17/00* | (2006.01) | |
| *G06T 7/507* | (2017.01) | |
| *G06T 7/586* | (2017.01) | |
| *G06T 7/593* | (2017.01) | |
| *G06T 7/292* | (2017.01) | |
| *G06K 9/20* | (2006.01) | |
| *G06K 9/32* | (2006.01) | |
| *G06F 3/01* | (2006.01) | |

(52) U.S. Cl.
CPC ...... *G06K 9/00375* (2013.01); *G06K 9/00711* (2013.01); *G06K 9/2036* (2013.01); *G06K 9/3241* (2013.01); *G06T 7/292* (2017.01); *G06T 7/507* (2017.01); *G06T 7/586* (2017.01); *G06T 7/593* (2017.01); *G06T 17/00* (2013.01); *G06F 3/017* (2013.01); *G06T 2207/10152* (2013.01); *G06T 2207/30196* (2013.01)

(58) Field of Classification Search
CPC ............. G06T 2207/10016; G06T 7/70; G06T 2200/04; G06T 2207/30196; G06T 2207/10012; G06T 7/344; G06T 17/00; G06T 7/11; G06T 7/593; G06T 2200/08; G06T 7/60; G06T 7/75; G06T 19/006; G06T 7/292; G06K 9/00201; G06K 9/00375; G06K 9/00355; G06K 9/3233; G06K 9/46; G06K 9/00382; G06K 9/6272; G06K 9/6878; G06K 2009/00395; G06K 9/00335; G06K 9/00389

See application file for complete search history.

(56) References Cited

U.S. PATENT DOCUMENTS

| | | | |
|---|---|---|---|
| 4,879,659 A | | 11/1989 | Bowlin et al. |
| 5,134,661 A | | 7/1992 | Reinsch |
| 5,282,067 A | | 1/1994 | Liu |
| 5,454,043 A | | 9/1995 | Freeman |
| 5,574,511 A | | 11/1996 | Yang et al. |
| 5,581,276 A | | 12/1996 | Cipolla et al. |
| 5,594,469 A | | 1/1997 | Freeman et al. |
| 5,742,263 A | | 4/1998 | Wang et al. |
| 5,900,863 A | | 5/1999 | Numazaki |
| 6,002,808 A | | 12/1999 | Freeman |
| 6,031,661 A | | 2/2000 | Tanaami |
| 6,072,494 A | | 6/2000 | Nguyen |
| 6,147,678 A | | 11/2000 | Kumar et al. |
| 6,154,558 A | | 11/2000 | Hsieh |
| 6,181,343 B1 | | 1/2001 | Lyons |
| 6,184,926 B1 | | 2/2001 | Khosravi et al. |
| 6,195,104 B1 | | 2/2001 | Lyons |
| 6,204,852 B1 | | 3/2001 | Kumar et al. |
| 6,252,598 B1 | | 6/2001 | Segen |
| 6,263,091 B1 | | 7/2001 | Jain et al. |
| 6,296,358 B1 | * | 10/2001 | Cornsweet ............. A61B 3/156 |
| | | | 351/206 |
| 6,463,402 B1 | | 10/2002 | Bennett et al. |
| 6,493,041 B1 | | 12/2002 | Hanko et al. |
| 6,498,628 B2 | | 12/2002 | Iwamura |
| 6,603,867 B1 | | 8/2003 | Sugino et al. |
| 6,661,918 B1 | | 12/2003 | Gordon et al. |
| 6,702,494 B2 | | 3/2004 | Dumler et al. |
| 6,798,628 B1 | | 9/2004 | Macbeth |
| 6,804,656 B1 | | 10/2004 | Rosenfeld et al. |
| 6,819,796 B2 | | 11/2004 | Hong et al. |
| 6,919,880 B2 | | 7/2005 | Morrison et al. |
| 6,950,534 B2 | | 9/2005 | Cohen et al. |
| 6,993,157 B1 | | 1/2006 | Oue et al. |
| 7,215,828 B2 | | 5/2007 | Luo |
| 7,244,233 B2 | | 7/2007 | Krantz et al. |
| 7,257,237 B1 | | 8/2007 | Luck et al. |
| 7,259,873 B2 | | 8/2007 | Sikora et al. |
| 7,308,112 B2 | * | 12/2007 | Fujimura ............ G06K 9/00355 |
| | | | 382/103 |
| 7,333,648 B2 | * | 2/2008 | Edic ...................... G06T 7/0012 |
| | | | 382/131 |
| 7,340,077 B2 | | 3/2008 | Gokturk et al. |
| 7,372,977 B2 | * | 5/2008 | Fujimura ............ G06K 9/00369 |
| | | | 382/103 |
| 7,519,223 B2 | | 4/2009 | Dehlin et al. |
| 7,532,206 B2 | | 5/2009 | Morrison et al. |
| 7,536,032 B2 | | 5/2009 | Bell |
| 7,542,586 B2 | | 6/2009 | Johnson |
| 7,598,942 B2 | | 10/2009 | Underkoffler et al. |
| 7,606,417 B2 | | 10/2009 | Steinberg et al. |
| 7,646,372 B2 | | 1/2010 | Marks et al. |
| 7,656,372 B2 | | 2/2010 | Sato et al. |
| 7,665,041 B2 | | 2/2010 | Wilson et al. |
| 7,692,625 B2 | | 4/2010 | Morrison et al. |
| 7,831,932 B2 | | 11/2010 | Josephsoon et al. |
| 7,840,031 B2 | | 11/2010 | Albertson et al. |
| 7,861,188 B2 | | 12/2010 | Josephsoon et al. |
| 7,940,885 B2 | | 5/2011 | Stanton et al. |
| 7,948,493 B2 | | 5/2011 | Klefenz et al. |
| 7,971,156 B2 | | 6/2011 | Albertson et al. |
| 8,005,263 B2 | * | 8/2011 | Fujimura ................ G06F 3/017 |
| | | | 379/52 |
| 8,064,704 B2 | | 11/2011 | Kim et al. |
| 8,085,339 B2 | | 12/2011 | Marks |
| 8,086,971 B2 | | 12/2011 | Radivojevic et al. |
| 8,111,239 B2 | | 2/2012 | Pryor et al. |
| 8,112,719 B2 | | 2/2012 | Hsu et al. |
| 8,185,176 B2 | | 5/2012 | Mangat et al. |
| 8,213,707 B2 | | 7/2012 | Li et al. |
| 8,244,233 B2 | | 8/2012 | Chang et al. |
| 8,290,208 B2 | | 10/2012 | Kurtz et al. |
| 8,471,848 B2 | | 6/2013 | Tschesnok |
| 8,514,221 B2 | | 8/2013 | King et al. |
| 8,638,989 B2 | | 1/2014 | Holz |
| 8,659,594 B2 | | 2/2014 | Kim et al. |
| 8,693,731 B2 | | 4/2014 | Holz et al. |
| 8,872,914 B2 | | 10/2014 | Gobush |
| 9,135,503 B2 | * | 9/2015 | Sundaresan ............. G06F 3/017 |
| 2002/0008211 A1 | | 1/2002 | Kask |
| 2002/0105484 A1 | | 8/2002 | Navab et al. |
| 2003/0053658 A1 | | 3/2003 | Pavlidis |
| 2003/0053659 A1 | | 3/2003 | Pavlidis et al. |
| 2003/0123703 A1 | | 7/2003 | Pavlidis et al. |
| 2003/0152289 A1 | | 8/2003 | Luo |
| 2003/0202697 A1 | | 10/2003 | Simard et al. |
| 2004/0125228 A1 | | 7/2004 | Dougherty |
| 2004/0145809 A1 | | 7/2004 | Brenner |
| 2004/0212725 A1 | | 10/2004 | Raskar |
| 2005/0131607 A1 | | 6/2005 | Breed |
| 2005/0168578 A1 | | 8/2005 | Gobush |
| 2005/0236558 A1 | | 10/2005 | Nabeshima et al. |
| 2006/0017807 A1 | | 1/2006 | Lee et al. |
| 2006/0072105 A1 | | 4/2006 | Wagner |
| 2006/0210112 A1 | | 9/2006 | Cohen et al. |
| 2006/0290950 A1 | | 12/2006 | Platt et al. |
| 2007/0042346 A1 | | 2/2007 | Weller |
| 2007/0130547 A1 | | 6/2007 | Boillot |
| 2007/0206719 A1 | | 9/2007 | Suryanarayanan et al. |
| 2007/0238956 A1 | | 10/2007 | Haras et al. |
| 2008/0019576 A1 | | 1/2008 | Senftner et al. |
| 2008/0056752 A1 | | 3/2008 | Denton et al. |
| 2008/0064954 A1 | | 3/2008 | Adams et al. |
| 2008/0106746 A1 | | 5/2008 | Shpunt et al. |

(56) References Cited

U.S. PATENT DOCUMENTS

| | | |
|---|---|---|
| 2008/0273764 A1 | 11/2008 | Scholl |
| 2008/0278589 A1 | 11/2008 | Thorn |
| 2008/0304740 A1 | 12/2008 | Sun et al. |
| 2008/0319356 A1 | 12/2008 | Cain et al. |
| 2009/0102840 A1 | 4/2009 | Li |
| 2009/0103780 A1 | 4/2009 | Nishihara et al. |
| 2009/0122146 A1 | 5/2009 | Zalewski et al. |
| 2009/0203993 A1 | 8/2009 | Mangat et al. |
| 2009/0203994 A1 | 8/2009 | Mangat et al. |
| 2009/0217211 A1 | 8/2009 | Hildreth et al. |
| 2009/0257623 A1 | 10/2009 | Tang et al. |
| 2009/0274339 A9 | 11/2009 | Cohen et al. |
| 2009/0309710 A1 | 12/2009 | Kakinami |
| 2010/0023015 A1 | 1/2010 | Park |
| 2010/0026963 A1 | 2/2010 | Faulstich |
| 2010/0027845 A1 | 2/2010 | Kim et al. |
| 2010/0046842 A1 | 2/2010 | Conwell |
| 2010/0053164 A1 | 3/2010 | Imai et al. |
| 2010/0058252 A1 | 3/2010 | Ko |
| 2010/0118123 A1 | 5/2010 | Freedman et al. |
| 2010/0125815 A1 | 5/2010 | Wang et al. |
| 2010/0158372 A1 | 6/2010 | Kim et al. |
| 2010/0177929 A1 | 7/2010 | Kurtz et al. |
| 2010/0201880 A1 | 8/2010 | Iwamura |
| 2010/0219934 A1 | 9/2010 | Matsumoto |
| 2010/0222102 A1 | 9/2010 | Rodriguez |
| 2010/0277411 A1 | 11/2010 | Yee et al. |
| 2010/0296698 A1 | 11/2010 | Lien et al. |
| 2010/0302357 A1 | 12/2010 | Hsu et al. |
| 2010/0306712 A1 | 12/2010 | Snook et al. |
| 2010/0309097 A1 | 12/2010 | Raviv et al. |
| 2011/0007072 A1 | 1/2011 | Khan et al. |
| 2011/0026765 A1 | 2/2011 | Ivanich et al. |
| 2011/0057875 A1 | 3/2011 | Shigeta et al. |
| 2011/0080470 A1 | 4/2011 | Kuno et al. |
| 2011/0093820 A1 | 4/2011 | Zhang et al. |
| 2011/0107216 A1 | 5/2011 | Bi |
| 2011/0115486 A1 | 5/2011 | Frohlich et al. |
| 2011/0119640 A1 | 5/2011 | Berkes et al. |
| 2011/0134112 A1 | 6/2011 | Koh et al. |
| 2011/0148875 A1 | 6/2011 | Kim et al. |
| 2011/0169726 A1 | 7/2011 | Holmdahl et al. |
| 2011/0173574 A1 | 7/2011 | Clavin et al. |
| 2011/0181509 A1 | 7/2011 | Rautiainen et al. |
| 2011/0205151 A1 | 8/2011 | Newton et al. |
| 2011/0213664 A1 | 9/2011 | Osterhout et al. |
| 2011/0228978 A1 | 9/2011 | Chen et al. |
| 2011/0234840 A1 | 9/2011 | Klefenz et al. |
| 2011/0267259 A1 | 11/2011 | Tidemand et al. |
| 2011/0286676 A1 | 11/2011 | El Dokor |
| 2011/0289455 A1 | 11/2011 | Reville et al. |
| 2011/0289456 A1 | 11/2011 | Reville et al. |
| 2011/0291925 A1 | 12/2011 | Israel et al. |
| 2011/0291988 A1 | 12/2011 | Bamji et al. |
| 2011/0296353 A1 | 12/2011 | Ahmed et al. |
| 2011/0299737 A1 | 12/2011 | Wang et al. |
| 2011/0304650 A1 | 12/2011 | Campillo et al. |
| 2011/0310007 A1 | 12/2011 | Margolis et al. |
| 2012/0038637 A1 | 2/2012 | Marks |
| 2012/0050157 A1 | 3/2012 | Latta et al. |
| 2012/0065499 A1 | 3/2012 | Chono |
| 2012/0068914 A1 | 3/2012 | Jacobsen et al. |
| 2012/0194517 A1 | 8/2012 | Izadi et al. |
| 2012/0250936 A1 | 10/2012 | Holmgren |
| 2012/0293667 A1 | 11/2012 | Baba et al. |
| 2013/0182079 A1 | 7/2013 | Holz |
| 2014/0139641 A1 | 5/2014 | Holz |
| 2014/0177913 A1 | 6/2014 | Holz |
| 2014/0222385 A1 | 8/2014 | Muenster et al. |
| 2014/0307920 A1 | 10/2014 | Holz |

FOREIGN PATENT DOCUMENTS

| | | |
|---|---|---|
| CN | 101729808 A | 6/2010 |
| CN | 101930610 A | 12/2010 |
| CN | 101951474 A | 1/2011 |
| CN | 102053702 A | 5/2011 |
| CN | 201859393 U | 6/2011 |
| CN | 102201121 A | 9/2011 |
| CN | 102236412 A | 11/2011 |
| DE | 4201934 A1 | 7/1993 |
| DE | 102007015495 A1 | 10/2007 |
| DE | 102007015497 B4 | 1/2014 |
| EP | 0999542 A1 | 5/2000 |
| EP | 1837665 A2 | 9/2007 |
| JP | 2009037594 A | 2/2009 |
| JP | 2011065652 A | 3/2011 |
| JP | 4906960 B2 | 3/2012 |
| KR | 101092909 B1 | 6/2011 |
| RU | 2422878 C1 | 6/2011 |
| TW | 200844871 A | 11/2008 |
| WO | 1994026057 A1 | 11/1994 |
| WO | 2004114220 A1 | 12/2004 |
| WO | 2006020846 A2 | 2/2006 |
| WO | 2007137093 A2 | 11/2007 |
| WO | 2010032268 A2 | 3/2010 |
| WO | 2010076622 A1 | 7/2010 |
| WO | 2011036618 A2 | 3/2011 |
| WO | 2011044680 A1 | 4/2011 |
| WO | 2011045789 A1 | 4/2011 |
| WO | 2011119154 A1 | 9/2011 |
| WO | 2012027422 A2 | 3/2012 |
| WO | 2013109608 A2 | 7/2013 |
| WO | 2013109609 A2 | 7/2013 |
| WO | 2015026707 A1 | 2/2015 |

OTHER PUBLICATIONS

Veldhuis et al., The 3D reconstruction of straight and curved pipes using digital line photogrammetry, ISPRS Journal of Photogrammetry and Remote Sensing, vol. 53, Issue 1, Feb. 1998 [retrieved Dec. 17, 2019], pp. 6-16. Retrieved: https://www.sciencedirect.com/science/article/pii/S0924271697000312 (Year: 1998).*

Olsson, K., et al., "Shape from Silhouette Scanner—Creating a Digital 3D Model of a Real Object by Analyzing Photos From Multiple Views," University of Linkoping, Sweden, Copyright VCG 2001, Retrieved from the Internet: <http://liu.diva-portal.org/smash/get/diva2:18671/FULLTEXT01> on Jun. 17, 2013, 52 pages.

Forbes, K., et al., "Using Silhouette Consistency Constraints to Build 3D Models," University of Cape Town, Copyright De Beers 2003, Retrieved from the internet: <http://www.dip.ee.uct.ac.za/~kforbes/Publications/Forbes2003Prasa.pdf> on Jun. 17, 2013, 6 pages.

May, S., et al., "Robust 3D-Mapping with Time-of-Flight Cameras," 2009 IEEE/RSJ International Conference on Intelligent Robots and Systems, Piscataway, NJ, USA, Oct. 10, 2009, pp. 1673-1678.

Kanhangad, V., et al., "A Unified Framework for Contactless Hand Verification," IEEE Transactions on Information Forensics and Security, IEEE, Piscataway, NJ, US., vol. 6, No. 3, Sep. 1, 2011, pp. 1014-1027.

Di Zenzo, S., et al., "Advances in Image Segmentation," Image and Vision Computing, Elsevier, Guildford, GBN, vol. 1, No. 1, Copyright Butterworth & Co Ltd., Nov. 1, 1983, pp. 196-210.

Davis et al., "Toward 3-D Gesture Recognition", International Journal of Pattern Recognition and Artificial Intelligence, vol. 13, No. 03, 1999, pp. 381-393.

Butail, S., et al., "Three-Dimensional Reconstruction of the Fast-Start Swimming Kinematics of Densely Schooling Fish," Journal of the Royal Society Interface, Jun. 3, 2011, retrieved from the Internet <http://www.ncbi.nlm.nih.gov/pubmed/21642367>, pp. 0, 1-12.

Kim, et al., "Development of an Orthogonal Double-Image Processing Algorithm to Measure Bubble," Department of Nuclear Engineering and Technology, Seoul National University Korea, vol. 39 No. 4, Published Jul. 6, 2007, pp. 313-326.

Barat et al., "Feature Correspondences From Multiple Views of Coplanar Ellipses", 2nd International Symposium on Visual Computing, Author Manuscript, 2006, 10 pages.

Cheikh et al., "Multipeople Tracking Across Multiple Cameras", International Journal on New Computer Architectures and Their Applications (IJNCAA), vol. 2, No. 1, 2012, pp. 23-33.

(56) References Cited

OTHER PUBLICATIONS

Kulesza, et al., "Arrangement of a Multi Stereo Visual Sensor System for a Human Activities Space," Source: Stereo Vision, Book edited by: Dr. Asim Bhatti, ISBN 978-953-7619-22-0, Copyright Nov. 2008, I-Tech, Vienna, Austria, www.intechopen.com, pp. 153-173.
Heikkila, J., "Accurate Camera Calibration and Feature Based 3-D Reconstruction from Monocular Image Sequences", Infotech Oulu and Department of Electrical Engineering, University of Oulu, 1997, 126 pages.
Arthington, et al., "Cross-section Reconstruction During Uniaxial Loading," Measurement Science and Technology, vol. 20, No. 7, Jun. 10, 2009, Retrieved from the Internet: http:iopscience.iop.org/0957-0233/20/7/075701, pp. 1-9.
Pedersini, et al., Accurate Surface Reconstruction from Apparent Contours, Sep. 5-8, 2000 European Signal Processing Conference EUSIPCO 2000, vol. 4, Retrieved from the Internet: http://home.deib.polimi.it/sarti/CV_and_publications.html, pp. 1-4.
Chung, et al., "International Journal of Computer Vision: RecoveringLSHGCs and SHGCs from Stereo" [on-line], Oct. 1996 [retrieved on Apr. 10, 2014], Kluwer Academic Publishers, vol. 20, issue 1-2, Retrieved from the Internet: http://link.springer.com/article/10.1007/BF00144116#, pp. 43-58.
Bardinet, et al., "Fitting of iso-Surfaces Using Superquadrics and Free-Form Deformations" [on-line], Jun. 24-25, 1994 [retrieved Jan. 9, 2014], 1994 Proceedings of IEEE Workshop on Biomedical Image Analysis, Retrieved from the Internet: http://ieeexplore.ieee.org/xpls/abs_all.jsp?arnumber=315882&tag=1, pp. 184-193.
Dombeck, D., et al., "Optical Recording of Action Potentials with Second-Harmonic Generation Microscopy," The Journal of Neuroscience, Jan. 28, 2004, vol. 24(4): pp. 999-1003.
U.S. Appl. No. 13/742,845—Office Action dated Jul. 22, 2013, 19 pages.
U.S. Appl. No. 13/742,845—Notice of Allowance dated Dec. 5, 2013, 11 pages.
U.S. Appl. No. 13/742,953—Office Action dated Jun. 14, 2013, 13 pages.
U.S. 13/742,953—Notice of Allowance dated Nov. 4, 2013, 14 pages.
PCT/US2013/021709—International Preliminary Report on Patentability dated Jul. 22, 2014, 22 pages.
U.S. Appl. No. 13/414,485—Office Action dated May 19, 2014, 16 pages.
U.S. Appl. No. 13/414,485—Final Office Action dated Feb. 12, 2015, 30 pages.
PCT/US2013/021709—International Search Report and Written Opinion dated Sep. 12, 2013, 22 pages.
PCT/US2013/021713—International Search Report and Written Opinion dated Sep. 11, 2013, 7 pages.
U.S. Appl. No. 13/414,485—Office Action dated Apr. 21, 2016, 24 pages.
U.S. Appl. No. 14/710,512—Notice of Allowance dated Apr. 28, 2016, 25 pages.
U.S. Appl. No. 13/742,845, Issue Notification, dated Mar. 19, 2014, 1 page (now U.S. Pat. No. 8,693,731).
U.S. Appl. No. 13/742,953—Office Action dated Jun. 14, 2013, 13 pages (non HBW).
U.S. Appl. No. 13/742,953—Notice of Allowance dated Nov. 4, 2013, 14 pages (non HBW).
U.S. Appl. No. 13/742,953, Issue Notification, dated Jan. 8, 2014, 1 pages (now U.S. Pat. No. 8,638,989).
U.S. Appl. No. 13/742,953, Notice of Allowance, dated Nov. 4, 2013, 9 pages (now U.S. Pat. No. 8,638,989).
U.S. Appl. No. 13/414,485—Office Action dated Nov. 4, 2016, 29 pages.
U.S. Appl. No. 14/723,370—Office Action dated Jan. 13, 2017, 33 pages.
PCT/US2013/021713—International Preliminary Report on Patentability dated Jul. 22, 2014, 13 pages (WO 2013/109609).
U.S. Appl. No. 13/742,953—Notice of Allowance dated Nov. 4, 2013, 14 pages.
U.S. Appl. No. 15/253,741—Office Action dated Jan. 13, 2014, 53 pages.

* cited by examiner $$C_1x^2 + C_2xy + C_3y^2 - (2C_1x_c + C_2y_c)x - (2C_3y_c + C_2x_c)y + (C_1x_c^2 + C_2x_cy_c + C_3y_c^2 - 1) = 0$$

$$C_1 = \frac{\cos^2\theta}{a^2} + \frac{\sin^2\theta}{b^2}$$

$$C_2 = -2\cos\theta\sin\theta\left(\frac{1}{a^2} - \frac{1}{b^2}\right)$$

$$C_3 = \frac{\sin^2\theta}{a^2} + \frac{\cos^2\theta}{b^2}$$

FIG. 10A $$r_{13} = \begin{bmatrix} A_1 & B_1 \\ A_3 & B_3 \end{bmatrix} \setminus \begin{bmatrix} -D_1 \\ -D_3 \end{bmatrix}$$

$$r_{23} = \begin{bmatrix} A_2 & B_2 \\ A_3 & B_3 \end{bmatrix} \setminus \begin{bmatrix} -D_2 \\ -D_3 \end{bmatrix}$$

$$r_{14} = \begin{bmatrix} A_1 & B_1 \\ A_4 & B_4 \end{bmatrix} \setminus \begin{bmatrix} -D_1 \\ -D_4 \end{bmatrix}$$

$$r_{24} = \begin{bmatrix} A_2 & B_2 \\ A_4 & B_4 \end{bmatrix} \setminus \begin{bmatrix} -D_2 \\ -D_4 \end{bmatrix}$$

FIG. 10B $$\mathbf{v} = \begin{bmatrix} G_2^2 & G_3^2 & G_4^2 \\ (G_2H_2)^2 & (G_3H_3)^2 & (G_4H_4)^2 \\ H_2^2 & H_3^2 & H_4^2 \end{bmatrix} \setminus \begin{bmatrix} 0 \\ 0 \\ 1 \end{bmatrix}$$

$$\mathbf{w} = \begin{bmatrix} G_2^2 & G_3^2 & G_4^2 \\ (G_2H_2)^2 & (G_3H_3)^2 & (G_4H_4)^2 \\ H_2^2 & H_3^2 & H_4^2 \end{bmatrix} \setminus \begin{bmatrix} 0 \\ 1 \\ 0 \end{bmatrix}$$

$$\mathbf{c1} = (r_{13}+r_{24})/2$$
$$\mathbf{c2} = (r_{14}+r_{23})/2$$
$$\delta 1 = c2_1 - c1_1$$
$$\delta 2 = c2_2 - c1_2$$
$$p = \delta 1/\delta 2$$
$$q = c1_1 - c1_2 * p$$
$$\mathbf{G} = \mathbf{A}p + \mathbf{B}$$
$$\mathbf{H} = \mathbf{A}q + \mathbf{D}$$

FIG. 10E $$Q_8 = 4A_1^2 n^2 v_{B2}^2 + 4 v_{B2} B_1^2 (1 - n^2 v_{A2}) \cdot (G_1(1-n^2 v_{A2})w_{B2} + n^2 v_{B2} w_{A2} + 2H_1 v_{B2})^2$$

FIG. 10F $$Q_7 = -(2(2n^2 v_{AB} w_{A2} + 4H_1 v_{AB} + 2G_1 n^2 v_{AB} w_{B2} + 2G_1(1-n^2 v_{A2})w_{AB})(G_1(1-n^2 v_{A2})w_{B2} + n^2 v_{B2} w_{A2} + 2H_1 v_{B2}) - 8A_1 B_1 n^2 v_{B2}^2 + 16A_1^2 n^2 v_{AB} v_{B2} + (4(2A_1 B_1(1-n^2 v_{A2}) + 2B_1 n^2 v_{AB}))v_{B2} + 8B_1^2(1 - n^2 v_{A2})v_{AB}$$

FIG. 10G $$Q_6 = -(2(2H_1 v_{B2} + 2H_1 v_{A2} + n^2 v_{A2} w_{A2} + n^2 v_{B2}(-2w_{AB} + w_{B2})) + G_1(n^2 v_{B2} + 1)w_{B2} + 4G_1 n^2 v_{AB} w_{AB} + G_1(1 - n^2 v_{A2})w_{AB}) \times (G_1(1-n^2 v_{A2})w_{B2} + n^2 v_{B2} w_{A2} + 2H_1 v_{B2})(2n^2 v_{AB} w_{A2} + 4H_1 v_{AB} + 2G_1 n^2 v_{AB} w_{B2} + 2G_1(1-n^2 v_{A2})w_{AB})^2 + 4B_1^2 n^2 v_{B2}^2 - 32A_1 B_1 n^2 v_{AB} v_{B2} + 4A_1^2 n^2(2v_{A2} v_{B2} + 4v_{AB}^2) + 4A_1^2 n^2 v_{B2}^2 + (4(A_1^2(1-n^2 v_{A2}) + 4A_1 B_1 n^2 v_{AB} + B_1^2(-n^2 v_{B2} + 1) + B_1^2(1-n^2 v_{A2}))v_{B2} + (8(2A_1 B_1(1 - n^2 v_{A2}) + 2B_1 n^2 v_{AB}))v_{AB} + 4B_1^2(1-n^2 v_{A2})v_{A2}$$

SYSTEMS AND METHODS OF LOCATING A CONTROL OBJECT APPENDAGE IN THREE DIMENSIONAL (3D) SPACE

CROSS-REFERENCE TO RELATED APPLICATION

This application is a continuation of U.S. patent application Ser. No. 14/723,370, filed May 27, 2015, entitled "SYSTEMS AND METHODS OF LOCATING A CONTROL OBJECT APPENDAGE IN THREE DIMENSIONAL (3D) SPACE", which is a continuation of U.S. patent application Ser. No. 13/724,357 filed Dec. 21, 2012, entitled "SYSTEMS AND METHODS FOR CAPTURING MOTION IN THREE-DIMENSIONAL SPACE", which is a continuation in part of U.S. patent application Ser. No. 13/414,485 filed Mar. 7, 2012, entitled "MOTION CAPTURE USING CROSS-SECTIONS OF AN OBJECT", which claims the benefit of U.S. Provisional Patent Application No. 61/587,554 filed Jan. 17, 2012, entitled "METHODS AND SYSTEMS FOR IDENTIFYING POSITION AND SHAPE OF OBJECTS IN THREE-DIMENSIONAL SPACE". Additionally, U.S. patent application Ser. No. 13/724,357 filed Dec. 21, 2012, entitled "SYSTEMS AND METHODS FOR CAPTURING MOTION IN THREE-DIMENSIONAL SPACE", claims priority to and the benefit of U.S. Provisional Patent Application No. 61/724,091 filed Nov. 8, 2012, entitled "SYSTEMS AND METHODS FOR CAPTURING MOTION IN THREE-DIMENSIONAL SPACE". The foregoing applications are incorporated herein by reference in their entireties.

FIELD OF THE INVENTION

The present invention relates, in general, to image analysis, and in particular embodiments to identifying shapes and capturing motions of objects in three-dimensional space.

BACKGROUND

Motion capture has numerous applications. For example, in filmmaking, digital models generated using motion capture can be used as the basis for the motion of computer-generated characters or objects. In sports, motion capture can be used by coaches to study an athlete's movements and guide the athlete toward improved body mechanics. In video games or virtual reality applications, motion capture can be used to allow a person to interact with a virtual environment in a natural way, e.g., by waving to a character, pointing at an object, or performing an action such as swinging a golf club or baseball bat.

The term "motion capture" refers generally to processes that capture movement of a subject in three-dimensional (3D) space and translate that movement into, for example, a digital model or other representation. Motion capture is typically used with complex subjects that have multiple separately articulating members whose spatial relationships change as the subject moves. For instance, if the subject is a walking person, not only does the whole body move across space, but the position of arms and legs relative to the person's core or trunk are constantly shifting. Motion capture systems are typically interested in modeling this articulation.

Most existing motion capture systems rely on markers or sensors worn by the subject while executing the motion and/or on the strategic placement of numerous cameras in the environment to capture images of the moving subject from different angles. Such systems tend to be expensive to construct. In addition, markers or sensors worn by the subject can be cumbersome and interfere with the subject's natural movement. Further, systems involving large numbers of cameras tend not to operate in real time, due to the volume of data that needs to be analyzed and correlated. Such considerations of cost, complexity and convenience have limited the deployment and use of motion capture technology.

Consequently, there is a need for an economical approach that captures the motion of objects in real time without attaching sensors or markers thereto.

SUMMARY

Embodiments of the present invention relate to methods and systems for capturing motion and/or determining the shapes and positions of one or more objects in 3D space using at least one cross-section thereof; the cross-section(s) may be obtained from, for example, reflections from the object or shadows cast by the object. In various embodiments, the 3D reflections or shadows captured using a camera are first sliced into multiple two-dimensional (2D) cross-sectional images. The cross-sectional position and shape (or "intersection region") of the 3D objects in each 2D slice may be determined based on the positions of one or more light sources used to illuminate the objects and the captured reflections or shadows. The 3D structure of the object may then be reconstructed by assembling a collection of the intersection regions obtained in the 2D slices. In some embodiments, the 2D intersection regions are identified based on "true" intersection points—i.e., points within the volume defined by the intersection of all light beams, which volume includes the object. These true intersection points may determined by the light sources and reflections or shadows—e.g., based on the number of reflection or shadow regions that they lie within or the locations of the geometric projection points calculated based on the positions of the light sources. In one embodiment, the light sources are arranged, for example, in a line or a plane such that the true intersection points are determined without identifying the actual locations thereof, this reduces the computational complexity, thereby increasing the processing speed. In some embodiments, the intersection region is split into a number of smaller intersection regions that can individually represent at least a portion of the reflections or shadows in the scene. Because determining each of the smaller intersection regions is computationally simpler than determining the entire intersection region, the processing time for obtaining the entire intersection region assembled from the individual smaller intersection regions is reduced (even if the smaller intersection regions are determined sequentially rather than in parallel). In various embodiments, the number of small split intersection regions that need to be identified is reduced by setting a criteria number U equal to the greatest number of intersection points in any intersection region; only regions or combinations of regions having a number of intersection points exceeding the criteria number U are further processed to identify the intersection regions therein.

In some embodiments, an image coordinate system using, for example, an imaging grid is incorporated into the system to easily define locations of the reflections or shadows. In one implementation, the camera includes multiple color filters placed on the light sensors to generate multiple images, each corresponding to a different color filter. Application of the 2D approaches described above to the color-specific images may then determine both the locations and colors of the objects.

Accordingly, in one aspect, the invention pertains to a method of identifying a position and shape of an object (e.g., a human, a human body part, or a handheld object such as a pencil or a scalpel) in 3D space. In representative embodiments, the method includes capturing an image generated by casting an output from one or more sources (e.g., a light source or a sonic source) onto the object; analyzing the image to computationally slice the object into multiple 2D slices, where each slice corresponds to a cross-section of the object; identifying shapes and positions of multiple cross-sections of the object based at least in part on the image and a location of the one or more sources; and reconstructing the position and shape of the object in 3D space based at least in part on the multiple identified cross-sectional shapes and positions of the object. The position and shape of the object in 3D space may be reconstructed based on correlations between the multiple 2D slices.

In various embodiments, the cross-sectional shape and position of the object is identified by selecting a collection of intersection points generated by analyzing a location of the one or more sources and positions of points in the image (e.g., a shadow of the object) associated with the 2D slice. The intersection points may be selected based on the total number source(s) employed. Alternatively, the intersection points may be selected based on locations of projection points associated with the intersection points, where the projection points are projections from the intersection points onto the 2D slice (e.g., where the projection is dictated by the position(s) of the source(s)). In some embodiments, the method further includes splitting the cross-section of the object into multiple regions and using each region to generate one or more portions of the shadow image of the 2D slice, and identifying the regions based on the shadow image of the 2D slice and the location of the one or more sources. A region may be established or recognized if the number of the intersection points is equal to or greater than a predetermined criteria number. Additionally, the intersection points may be selected based on the location of the source(s) and the size of the image cross-section. The image may include reflections from the object and the intersection points may be selected based on time-of-flight data using a time-of-flight camera. In one implementation, the selected collection of intersection points in a first 2D slice is reused in a second 2D slice. In addition, the image may be generated by casting light from multiple light sources, aligned in a line or in a plane, onto the object.

In one embodiment, the method includes defining a 3D model of the object and reconstructing the position and shape of the object in 3D space based on the 3D model. In another embodiment, the method includes defining coordinates of the image. In one implementation, the image is separated into multiple primary images each including a color; various colors on the object are identified based on the primary images.

In various embodiments, the method includes manipulating one or more virtual objects displayed on a device based on the identified position and shape of the object. The device may be a head-mounted device or a TV. In one embodiment, the identified position and shape of the object is used to manipulate the virtual object via wireless cell phone communication. In some embodiments, the method further includes authenticating a user based on the detected shape of the object and/or the detected motion of the object and subsequent matching thereof to data in a database record corresponding to the user.

In another aspect, the invention relates to a system for identifying a position and shape of an object in 3D space. In various embodiments, the system includes one or more cameras (e.g., a time-of-flight camera) oriented toward a field of view; one or more sources (e.g., a light source or a sonic source) to direct illumination onto the object in the field of view; and an image analyzer coupled to the camera and the source and configured to operate the camera to capture one or more images of the object and identify a position and shape of the object in 3D space based on the captured image and a location of the source.

In one implementation, the one or more light sources include multiple light sources each aligned in a line or in a plane. Additionally, the system may include multiple filters placed on light sensors of the camera to generate multiple images, each of which corresponds to a color filter. In one embodiment, the image analyzer is further configured to (i) slice the object into multiple 2D slices each corresponding to a cross-section of the object, (ii) identify a shape and position of the object based at least in part on an image captured by the camera and a location of the one or more light source, and (iii) reconstruct the position and shape of the object in 3D space based at least in part on the multiple identified cross-sectional shapes and positions of the object. In some embodiments, the image analyzer is further configured to define a 3D model of the object and reconstruct the position and shape of the object in 3D space based on the 3D model.

In various embodiments, the system further includes a secondary device (e.g., a head-mounted device or a mobile device) operatively connected to the system. The secondary device may be an authentication server for authenticating a user based on a shape and/or a jitter of the user's hand detected by the image analyzer.

Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which:

FIG. 4A is a top view of a slice. FIG. 4B illustrates projecting edge points from an image plane to a vantage point to define tangent lines. FIG. 4C illustrates fitting an ellipse to tangent lines as defined in FIG. 4B;

FIG. 8 sets forth a general equation for an ellipse in the xy plane;

FIGS. 10A, 10B, 10C, 10D, 10E, 10F, 10G, 10H, 10I, 10J, 10K, 10L, 10M and 10N set forth equations that can be solved to fit an ellipse to four tangent lines according to an embodiment of the present invention;

DETAILED DESCRIPTION

Embodiments of the present invention relate to methods and systems for capturing motion and/or determining position of an object using small amounts of information. For example, an outline of an object's shape, or silhouette, as seen from a particular vantage point can be used to define tangent lines to the object from that vantage point in various planes, referred to herein as "slices." Using as few as two different vantage points, four (or more) tangent lines from the vantage points to the object can be obtained in a given slice. From these four (or more) tangent lines, it is possible to determine the position of the object in the slice and to approximate its cross-section in the slice, e.g., using one or more ellipses or other simple closed curves. As another example, locations of points on an object's surface in a particular slice can be determined directly (e.g., using a time-of-flight camera), and the position and shape of a cross-section of the object in the slice can be approximated by fitting an ellipse or other simple closed curve to the points. Positions and cross-sections determined for different slices can be correlated to construct a 3D model of the object, including its position and shape. A succession of images can be analyzed using the same technique to model motion of the object. Motion of a complex object that has multiple separately articulating members (e.g., a human hand) can be modeled using techniques described herein.

In some embodiments, the silhouettes of an object are extracted from one or more images of the object that reveal information about the object as seen from different vantage points. While silhouettes can be obtained using a number of different techniques, in some embodiments, the silhouettes are obtained by using cameras to capture images of the object and analyzing the images to detect object edges.

Figure 1:
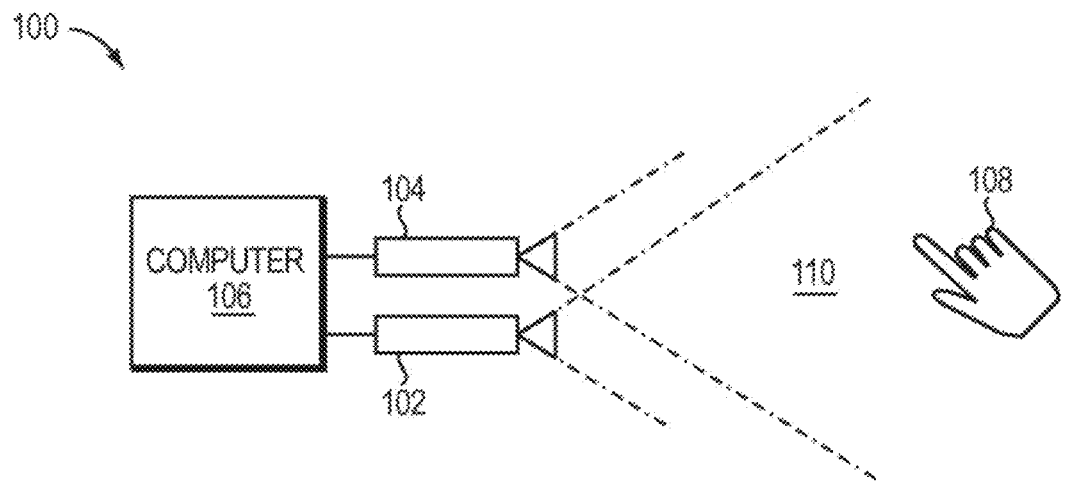
FIG. 1 is a simplified illustration of a motion capture system according to an embodiment of the present invention.

FIG. 1 is a simplified illustration of a motion capture system 100 according to an embodiment of the present invention. System 100 includes two cameras 102, 104 arranged such that their fields of view (indicated by broken lines) overlap in region 110. Cameras 102 and 104 are coupled to provide image data to a computer 106. Computer 106 analyzes the image data to determine the 3D position and motion of an object, e.g., a hand 108, that moves in the field of view of cameras 102, 104.

Cameras 102, 104 can be any type of camera, including visible-light cameras, infrared (IR) cameras, ultraviolet cameras or any other devices (or combination of devices) that are capable of capturing an image of an object and representing that image in the form of digital data. Cameras 102, 104 are preferably capable of capturing video images (i.e., successive image frames at a constant rate of at least 15 frames per second), although no particular frame rate is required. The particular capabilities of cameras 102, 104 are not critical to the invention, and the cameras can vary as to frame rate, image resolution (e.g., pixels per image), color or intensity resolution (e.g., number of bits of intensity data per pixel), focal length of lenses, depth of field, etc. In general, for a particular application, any cameras capable of focusing on objects within a spatial volume of interest can be used. For instance, to capture motion of the hand of an otherwise stationary person, the volume of interest might be a meter on a side. To capture motion of a running person, the volume of interest might be tens of meters in order to observe several strides (or the person might run on a treadmill, in which case the volume of interest can be considerably smaller).

The cameras can be oriented in any convenient manner. In the embodiment shown, respective optical axes 112, 114 of cameras 102 and 104 are parallel, but this is not required. As described below, each camera is used to define a "vantage point" from which the object is seen, and it is required only that a location and view direction associated with each vantage point be known, so that the locus of points in space that project onto a particular position in the camera's image plane can be determined. In some embodiments, motion capture is reliable only for objects in area 110 (where the fields of view of cameras 102, 104 overlap), and cameras 102, 104 may be arranged to provide overlapping fields of view throughout the area where motion of interest is expected to occur.

Figure 2:
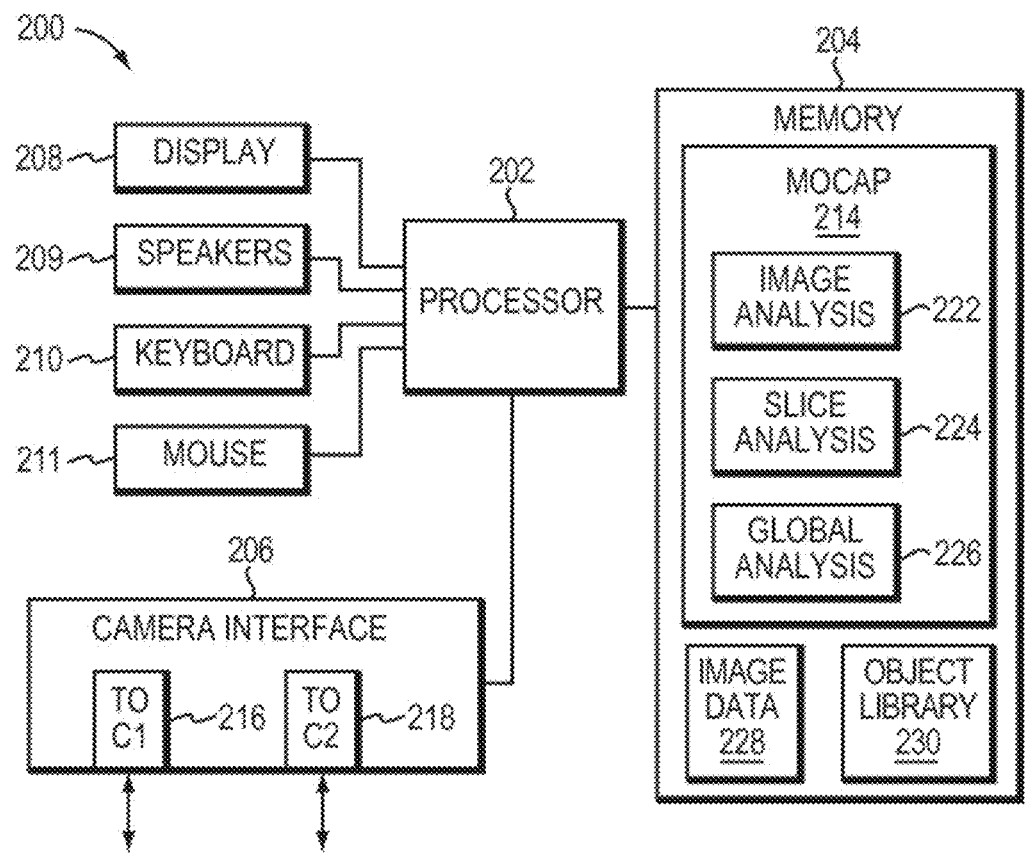
FIG. 2 is a simplified block diagram of a computer system that can be used according to an embodiment of the present invention.

In FIG. 1 and other examples described herein, object 108 is depicted as a hand. The hand is used only for purposes of illustration, and it is to be understood that any other object can be the subject of motion capture analysis as described herein. Computer 106 can be any device that is capable of processing image data using techniques described herein. FIG. 2 is a simplified block diagram of computer system 200 implementing computer 106 according to an embodiment of the present invention. Computer system 200 includes a processor 202, a memory 204, a camera interface 206, a display 208, speakers 209, a keyboard 210, and a mouse 211.

Processor 202 can be of generally conventional design and can include, e.g., one or more programmable microprocessors capable of executing sequences of instructions. Memory 204 can include volatile (e.g., DRAM) and nonvolatile (e.g., flash memory) storage in any combination. Other storage media (e.g., magnetic disk, optical disk) can also be provided. Memory 204 can be used to store instructions to be executed by processor 202 as well as input and/or output data associated with execution of the instructions.

Camera interface 206 can include hardware and/or software that enables communication between computer system 200 and cameras such as cameras 102, 104 of FIG. 1. Thus, for example, camera interface 206 can include one or more data ports 216, 218 to which cameras can be connected, as well as hardware and/or software signal processors to modify data signals received from the cameras (e.g., to reduce noise or reformat data) prior to providing the signals as inputs to a conventional motion-capture ("mocap") program 214 executing on processor 202. In some embodiments, camera interface 206 can also transmit signals to the cameras, e.g., to activate or deactivate the cameras, to control camera settings (frame rate, image quality, sensitivity, etc.), or the like. Such signals can be transmitted, e.g., in response to control signals from processor 202, which may in turn be generated in response to user input or other detected events.

In some embodiments, memory 204 can store mocap program 214, which includes instructions for performing motion capture analysis on images supplied from cameras connected to camera interface 206. In one embodiment, mocap program 214 includes various modules, such as an image analysis module 222, a slice analysis module 224, and a global analysis module 226. Image analysis module 222 can analyze images, e.g., images captured via camera interface 206, to detect edges or other features of an object. Slice analysis module 224 can analyze image data from a slice of an image as described below, to generate an approximate cross-section of the object in a particular plane. Global analysis module 226 can correlate cross-sections across different slices and refine the analysis. Examples of operations that can be implemented in code modules of mocap program 214 are described below.

Memory 204 can also include other information used by mocap program 214; for example, memory 204 can store image data 228 and an object library 230 that can include canonical models of various objects of interest. As described below, an object being modeled can be identified by matching its shape to a model in object library 230.

Display 208, speakers 209, keyboard 210, and mouse 211 can be used to facilitate user interaction with computer system 200. These components can be of generally conventional design or modified as desired to provide any type of user interaction. In some embodiments, results of motion capture using camera interface 206 and mocap program 214 can be interpreted as user input. For example, a user can perform hand gestures that are analyzed using mocap program 214, and the results of this analysis can be interpreted as an instruction to some other program executing on processor 200 (e.g., a web browser, word processor or the like). Thus, by way of illustration, a user might be able to use upward or downward swiping gestures to "scroll" a webpage currently displayed on display 208, to use rotating gestures to increase or decrease the volume of audio output from speakers 209, and so on.

It will be appreciated that computer system 200 is illustrative and that variations and modifications are possible. Computers can be implemented in a variety of form factors, including server systems, desktop systems, laptop systems, tablets, smart phones or personal digital assistants, and so on. A particular implementation may include other functionality not described herein, e.g., wired and/or wireless network interfaces, media playing and/or recording capability, etc. In some embodiments, one or more cameras may be built into the computer rather than being supplied as separate components.

While computer system 200 is described herein with reference to particular blocks, it is to be understood that the blocks are defined for convenience of description and are not intended to imply a particular physical arrangement of component parts. Further, the blocks need not correspond to physically distinct components. To the extent that physically distinct components are used, connections between components (e.g., for data communication) can be wired and/or wireless as desired.

An example of a technique for motion capture using the system of FIGS. 1 and 2 will now be described. In this embodiment, cameras 102, 104 are operated to collect a sequence of images of an object 108. The images are time correlated such that an image from camera 102 can be paired with an image from camera 104 that was captured at the same time (within a few milliseconds). These images are then analyzed, e.g., using mocap program 214, to determine the object's position and shape in 3D space. In some embodiments, the analysis considers a stack of 2D cross-sections through the 3D spatial field of view of the cameras. These cross-sections are referred to herein as "slices."

Figure 3A:
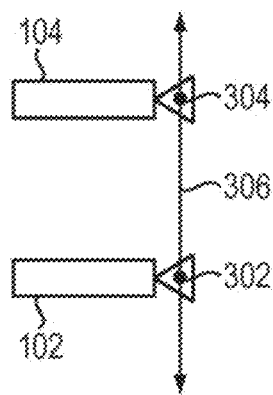
FIGS. 3A (top view) and 3B (side view) are conceptual illustrations of how slices are defined in a field of view according to an embodiment of the present invention.
Figure 3B:
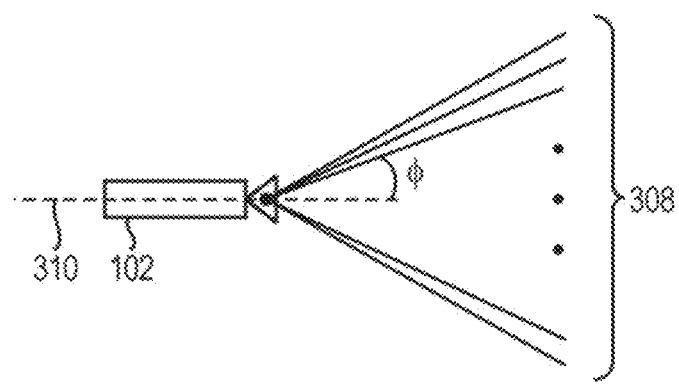

FIGS. 3A and 3B are conceptual illustrations of how slices are defined in a field of view according to an embodiment of the present invention. FIG. 3A shows, in top view, cameras 102 and 104 of FIG. 1. Camera 102 defines a vantage point 302, and camera 104 defines a vantage point 304. Line 306 joins vantage points 302 and 304. FIG. 3B shows a side view of cameras 102 and 104; in this view, camera 104 happens to be directly behind camera 102 and thus occluded; line 306 is perpendicular to the plane of the drawing. (It should be noted that the designation of these views as "top" and "side" is arbitrary; regardless of how the cameras are actually oriented in a particular setup, the "top" view can be understood as a view looking along a direction normal to the plane of the cameras, while the "side" view is a view in the plane of the cameras.)

An infinite number of planes can be drawn through line 306. A "slice" can be any one of those planes for which at least part of the plane is in the field of view of cameras 102 and 104. Several slices 308 are shown in FIG. 3B. (Slices 308 are seen edge-on; it is to be understood that they are 2D planes and not 1-D lines.) For purposes of motion capture analysis, slices can be selected at regular intervals in the field of view. For example, if the received images include a fixed number of rows of pixels (e.g., 1080 rows), each row can be a slice, or a subset of the rows can be used for faster processing. Where a subset of the rows is used, image data from adjacent rows can be averaged together, e.g., in groups of 2-3.

Figure 4A:
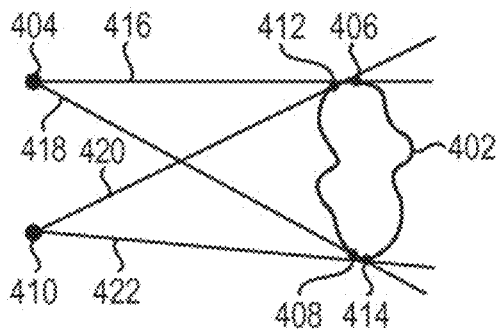
FIGS. 4A, 4B and 4C are top views illustrating an analysis that can be performed on a given slice according to an embodiment of the present invention.
Figure 4B:
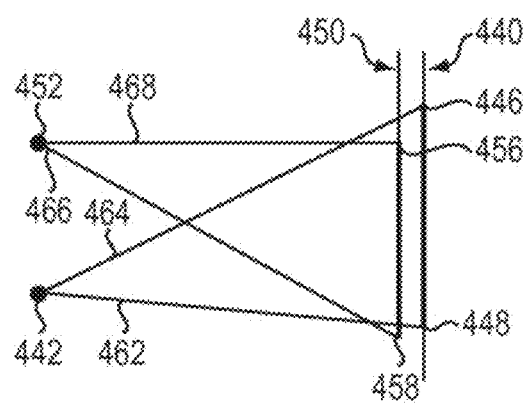
Figure 4C:
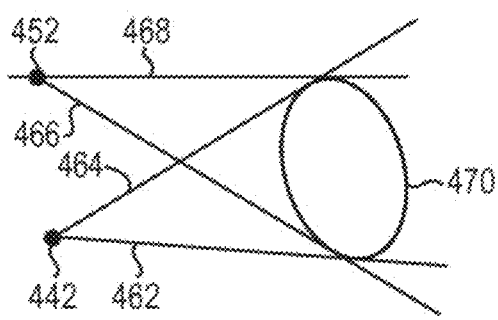

FIGS. 4A-4C illustrate an analysis that can be performed on a given slice. FIG. 4A is a top view of a slice as defined above, corresponding to an arbitrary cross-section 402 of an object. Regardless of the particular shape of cross-section 402, the object as seen from a first vantage point 404 has a "left edge" point 406 and a "right edge" point 408. As seen from a second vantage point 410, the same object has a "left edge" point 412 and a "right edge" point 414. These are in general different points on the boundary of object 402. A tangent line can be defined that connects each edge point and the associated vantage point. For example, FIG. 4A also shows that tangent line 416 can be defined through vantage point 404 and left edge point 406; tangent line 418 through vantage point 404 and right edge point 408; tangent line 420 through vantage point 410 and left edge point 412; and tangent line 422 through vantage point 410 and right edge point 414.

It should be noted that all points along any one of tangent lines 416, 418, 420, 422 will project to the same point on an image plane. Therefore, for an image of the object from a given vantage point, a left edge point and a right edge point can be identified in the image plane and projected back to the vantage point, as shown in FIG. 4B, which is another top view of a slice, showing the image plane for each vantage point. Image 440 is obtained from vantage point 442 and shows left edge point 446 and right edge point 448. Image 450 is obtained from vantage point 452 and shows left edge point 456 and right edge point 458. Tangent lines 462, 464, 466, 468 can be defined as shown. Given the tangent lines of FIG. 4B, the location in the slice of an elliptical cross-section can be determined, as illustrated in FIG. 4C, where ellipse 470 has been fit to tangent lines 462, 464, 466, 468 of FIG. 4B.

Figure 5:
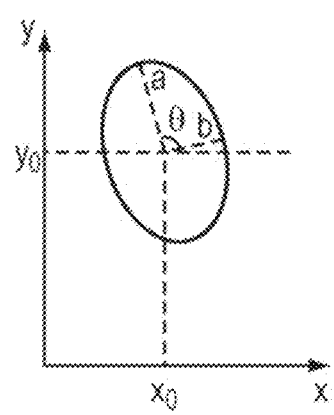
FIG. 5 graphically illustrates an ellipse in the xy plane characterized by five parameters.

In general, as shown in FIG. 5, an ellipse in the xy plane can be characterized by five parameters: the x and y coordinates of the center $(x_C, y_C)$, the semimajor axis (a), the semiminor axis (b), and a rotation angle (θ) (e.g., the angle of the semimajor axis relative to the x axis). With only four tangents, as is the case in FIG. 4C, the ellipse is underdetermined. However, an efficient process for estimating the ellipse in spite of this has been developed. In various embodiments as described below, this involves making an initial working assumption (or "guess") as to one of the parameters and revisiting the assumption as additional information is gathered during the analysis. This additional information can include, for example, physical constraints based on properties of the cameras and/or the object.

In some embodiments, more than four tangents to an object may be available for some or all of the slices, e.g., because more than two vantage points are available. An elliptical cross-section can still be determined, and the process in some instances is somewhat simplified as there is no need to assume a parameter value. In some instances, the additional tangents may create additional complexity. Examples of processes for analysis using more than four tangents are described below and in the '554 application noted above.

In some embodiments, fewer than four tangents to an object may be available for some or all of the slices, e.g., because an edge of the object is out of range of the field of view of one camera or because an edge was not detected. A slice with three tangents can be analyzed. For example, using two parameters from an ellipse fit to an adjacent slice (e.g., a slice that had at least four tangents), the system of equations for the ellipse and three tangents is sufficiently determined that it can be solved. As another option, a circle can be fit to the three tangents; defining a circle in a plane requires only three parameters (the center coordinates and the radius), so three tangents suffice to fit a circle. Slices with fewer than three tangents can be discarded or combined with adjacent slices.

In some embodiments, each of a number of slices is analyzed separately to determine the size and location of an elliptical cross-section of the object in that slice. This provides an initial 3D model (specifically, a stack of elliptical cross-sections), which can be refined by correlating the cross-sections across different slices. For example, it is expected that an object's surface will have continuity, and discontinuous ellipses can accordingly be discounted. Further refinement can be obtained by correlating the 3D model with itself across time, e.g., based on expectations related to continuity in motion and deformation.

Figure 6A:
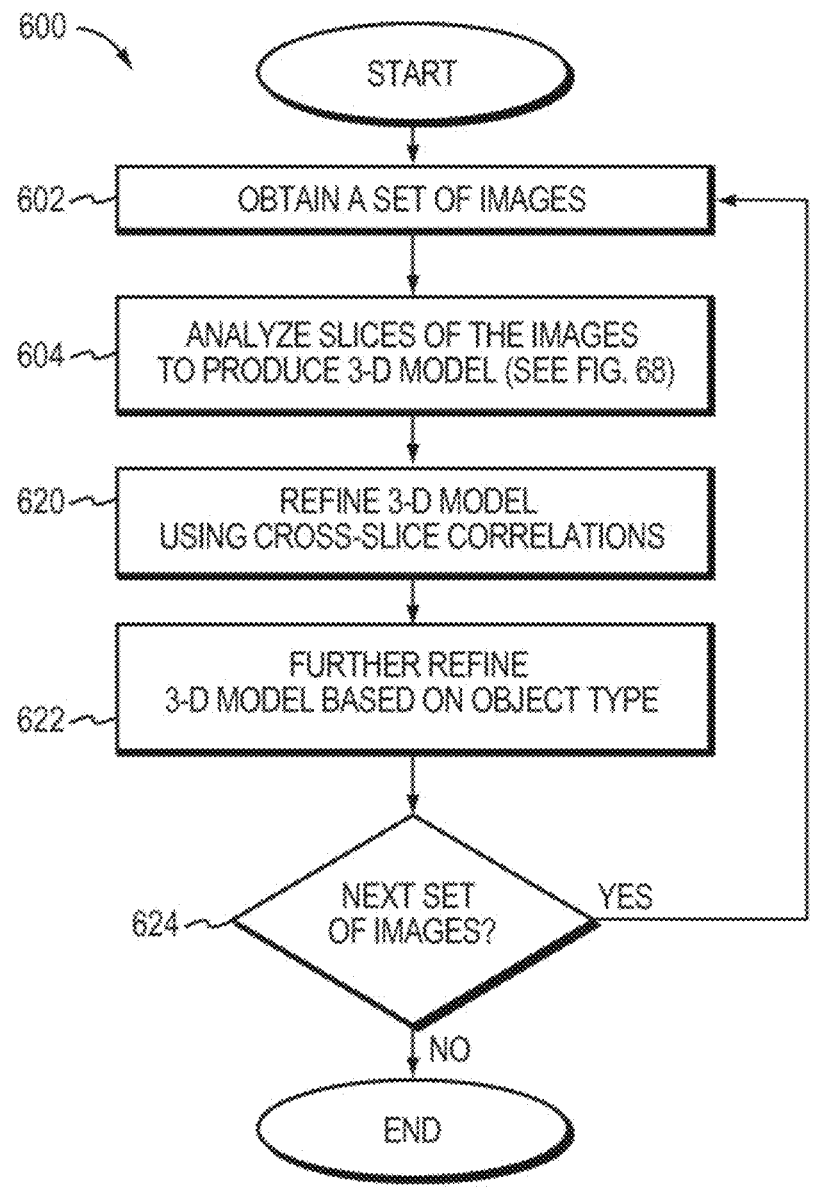
FIGS. 6A and 6B provide a flow diagram of a motion-capture process according to an embodiment of the present invention.
Figure 6B:
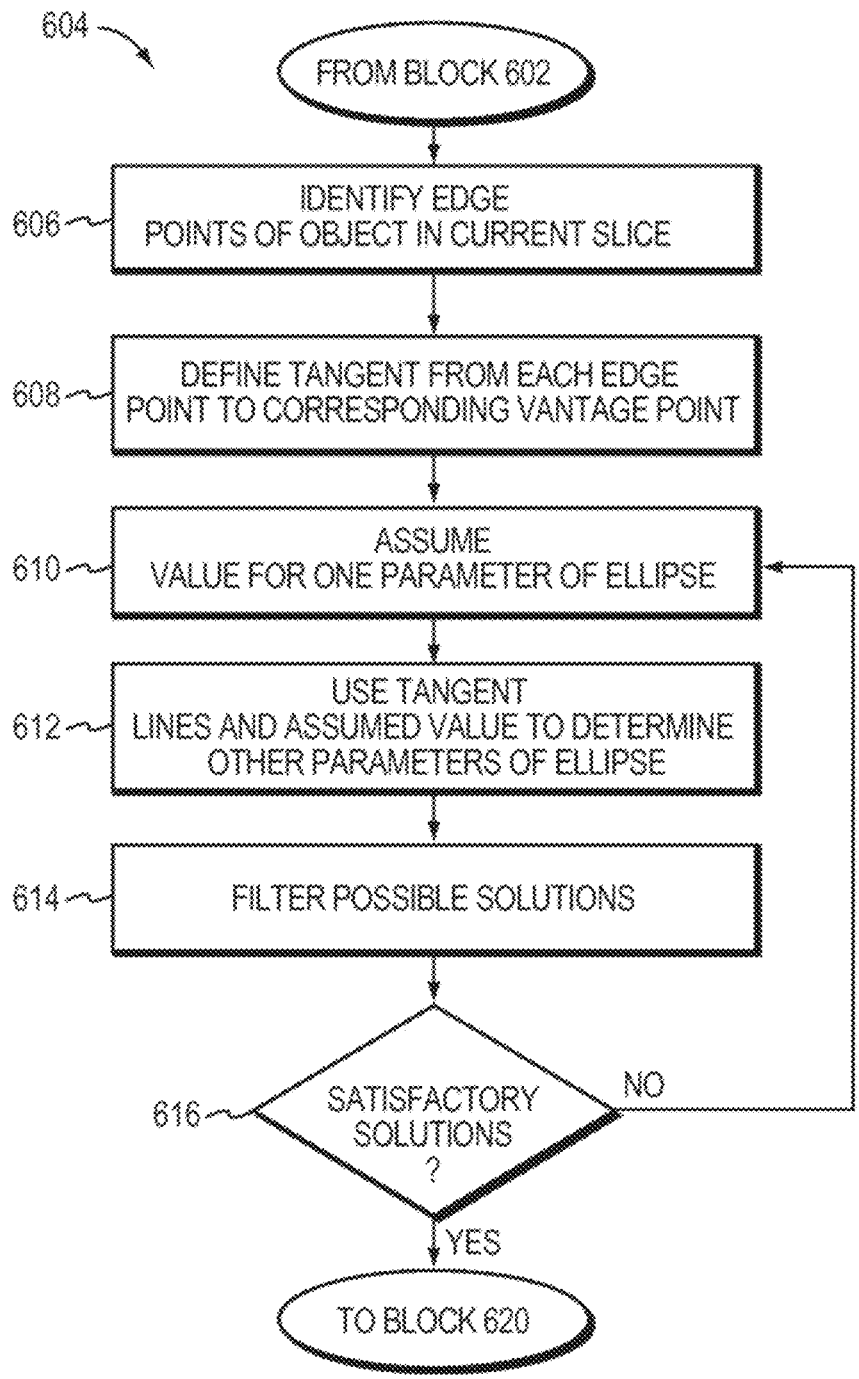

A further understanding of the analysis process can be had by reference to FIGS. 6A-6B, which provide a flow diagram of a motion-capture process 600 according to an embodiment of the present invention. Process 600 can be implemented, e.g., in mocap program 214 of FIG. 2.

At block 602, a set of images—e.g., one image from each camera 102, 104 of FIG. 1—is obtained. In some embodiments, the images in a set are all taken at the same time (or within a few milliseconds), although a precise timing is not required. The techniques described herein for constructing an object model assume that the object is in the same place in all images in a set, which will be the case if images are taken at the same time. To the extent that the images in a set are taken at different times, motion of the object may degrade the quality of the result, but useful results can be obtained as long as the time between images in a set is small enough that the object does not move far, with the exact limits depending on the particular degree of precision desired.

At block 604, each slice is analyzed. FIG. 6B illustrates a per-slice analysis that can be performed at block 604. Referring to FIG. 6B, at block 606, edge points of the object in a given slice are identified in each image in the set. For example, edges of an object in an image can be detected using conventional techniques, such as contrast between adjacent pixels or groups of pixels. In some embodiments, if no edge points are detected for a particular slice (or if only one edge point is detected), no further analysis is performed on that slice. In some embodiments, edge detection can be performed for the image as a whole rather than on a per-slice basis.

At block 608, assuming enough edge points were identified, a tangent line from each edge point to the corresponding vantage point is defined, e.g., as shown in FIG. 4C and described above. At block 610 an initial assumption as to the value of one of the parameters of an ellipse is made, to reduce the number of free parameters from five to four. In some embodiments, the initial assumption can be, e.g., the semimajor axis (or width) of the ellipse. Alternatively, an assumption can be made as to eccentricity (ratio of semimajor axis to semiminor axis), and that assumption also reduces the number of free parameters from five to four. The assumed value can be based on prior information about the object. For example, if previous sequential images of the object have already been analyzed, it can be assumed that the dimensions of the object do not significantly change from image to image. As another example, if it is assumed that the object being modeled is a particular type of object (e.g., a hand), a parameter value can be assumed based on typical dimensions for objects of that type (e.g., an average cross-sectional dimension of a palm or finger). An arbitrary assumption can also be used, and any assumption can be refined through iterative analysis as described below.

Figure 7:
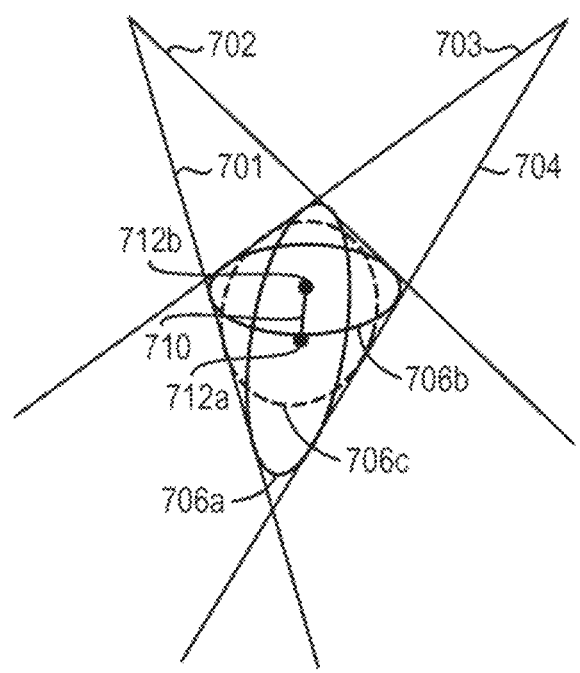
FIG. 7 graphically illustrates a family of ellipses that can be constructed from four tangent lines.

At block 612, the tangent lines and the assumed parameter value are used to compute the other four parameters of an ellipse in the plane. For example, as shown in FIG. 7, four tangent lines 701, 702, 703, 704 define a family of inscribed ellipses 706 including ellipses 706a, 706b, and 706c, where each inscribed ellipse 706 is tangent to all four of lines 701-704. Ellipse 706a and 706b represent the "extreme" cases (i.e., the most eccentric ellipses that are tangent to all four of lines 701-704. Intermediate between these extremes are an infinite number of other possible ellipses, of which one example, ellipse 706c, is shown (dashed line).

The solution process selects one (or in some instances more than one) of the possible inscribed ellipses 706. In one embodiment, this can be done with reference to the general equation for an ellipse shown in FIG. 8. The notation follows that shown in FIG. 5, with (x, y) being the coordinates of a point on the ellipse, ($x_C$, $y_C$) the center, a and b the axes, and θ the rotation angle. The coefficients $C_1$, $C_2$ and $C_3$ are defined in terms of these parameters, as shown in FIG. 8.

Figure 9:
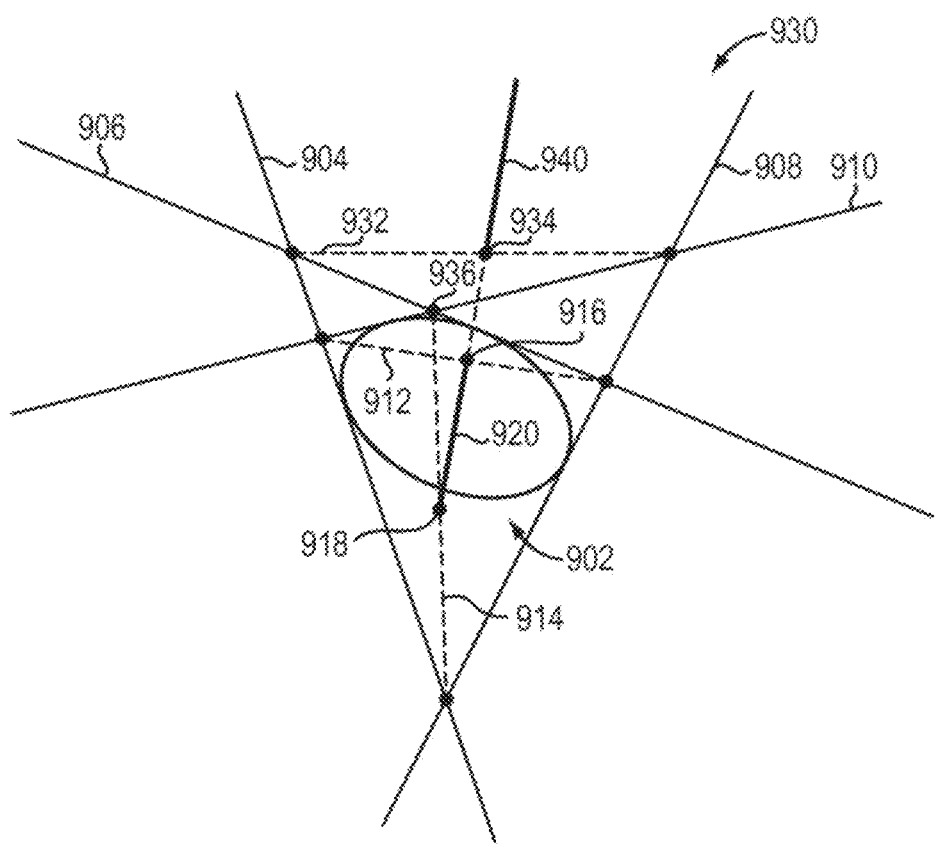
FIG. 9 graphically illustrates how a centerline can be found for an intersection region with four tangent lines according to an embodiment of the present invention.

The number of free parameters can be reduced based on the observation that the centers ($x_C$, $y_C$) of all the ellipses in family 706 line on a line segment 710 (also referred to herein as the "centerline") between the center of ellipse 706a (shown as point 712a) and the center of ellipse 706b (shown as point 712b). FIG. 9 illustrates how a centerline can be found for an intersection region. Region 902 is a "closed" intersection region; that is, it is bounded by tangents 904, 906, 908, 910. The centerline can be found by identifying diagonal line segments 912, 914 that connect the opposite corners of region 902, identifying the midpoints 916, 918 of these line segments, and identifying the line segment 920 joining the midpoints as the centerline.

Region 930 is an "open" intersection region; that is, it is only partially bounded by tangents 904, 906, 908, 910. In this case, only one diagonal, line segment 932, can be defined. To define a centerline for region 930, centerline 920 from closed intersection region 902 can be extended into region 930 as shown. The portion of extended centerline 920 that is beyond line segment 932 is centerline 940 for region 930. In general, for any given set of tangent lines, both region 902 and region 930 can be considered during the solution process. (Often, one of these regions is outside the field of view of the cameras and can be discarded at a later stage.) Defining the centerline reduces the number of free parameters from five to four because $y_C$ can be expressed as a (linear) function of $x_C$ (or vice versa), based solely on the four tangent lines. However, for every point ($x_C$, $y_C$) on the centerline, a set of parameters {θ, a, b} can be found for an inscribed ellipse. To reduce this to a set of discrete solutions, an assumed parameter value can be used. For example, it can be assumed that the semimajor axis a has a fixed value $a_0$. Then, only solutions {θ, a, b} that satisfy $a=a_0$ are accepted.

In one embodiment, the ellipse equation of FIG. 8 is solved for θ, subject to the constraints that: (1) ($x_C$, $y_C$) must lie on the centerline determined from the four tangents (i.e., either centerline 920 or centerline 940 of FIG. 9); and (2) a is fixed at the assumed value $a_0$. The ellipse equation can either be solved for θ analytically or solved using an iterative numerical solver (e.g., a Newtonian solver as is known in the art). An analytic solution can be obtained by writing an equation for the distances to the four tangent lines given a $y_C$ position, then solving for the value of $y_C$ that corresponds to the desired radius parameter $a=a_0$. One analytic solution is illustrated in the equations of FIGS. 10A-10D. Shown in FIG. 10A are equations for four tangent lines in the xy plane (the slice). Coefficients $A_i$, $B_i$ and $D_i$ (for i=1 to 4) can be determined from the tangent lines identified in an image slice as described above. FIG. 10B illustrates the definition of four column vectors $r_{12}$, $r_{23}$, $r_{14}$ and $r_{24}$ from the coefficients of FIG. 10A. The "\" operator here denotes matrix left division, which is defined for a square matrix M and a column vector v such that M\v=r, where r is the column vector that satisfies Mr=v. FIG. 10C illustrates the definition of G and H, which are four-component vectors from the vectors of tangent coefficients A, B and D and scalar quantities p and q, which are defined using the column vectors $r_{12}$, $r_{23}$, $r_{14}$ and $r_{24}$ from FIG. 10B. FIG. 10D illustrates the definition of six scalar quantities $v_{A2}$, $v_{AB}$, $v_{B2}$, $w_{A2}$, $w_{AB}$, and $w_{B2}$ in terms of the components of vectors G and H of FIG. 10C.

Using the parameters defined in FIGS. 10A-10D, solving for θ is accomplished by solving the eighth-degree polynomial equation shown in FIG. 10E for t, where the coefficients $Q_i$ (for i=0 to 8) are defined as shown in FIGS. 10F-10N. The parameters $A_1$, $B_1$, $G_1$, $H_1$, $v_{A2}$, $v_{AB}$, $v_{B2}$, $w_{A2}$, $w_{AB}$, and $w_{B2}$ used in FIGS. 10F-10N are defined as shown in FIGS. 10A-10D. The parameter n is the assumed semimajor axis (in other words, $a_0$). Once the real roots t are known, the possible values of θ are defined as θ=a tan(t).

As it happens, the equation of FIGS. 10E-10N has at most three real roots; thus, for any four tangent lines, there are at most three possible ellipses that are tangent to all four lines and satisfy the $a=a_0$ constraint. (In some instances, there may be fewer than three real roots.) For each real root θ, the corresponding values of ($x_C$, $y_C$) and b can be readily determined. Depending on the particular inputs, zero or more solutions will be obtained; for example, in some instances, three solutions can be obtained for a typical configuration of tangents. Each solution is completely characterized by the parameters {θ, $a=a_0$, b, ($x_C$, $y_C$)}.

Referring again to FIG. 6B, at block 614, the solutions are filtered by applying various constraints based on known (or inferred) physical properties of the system. For example, some solutions would place the object outside the field of view of the cameras, and such solutions can readily be rejected. As another example, in some embodiments, the type of object being modeled is known (e.g., it can be known that the object is or is expected to be a human hand). Techniques for determining object type are described below; for now, it is noted that where the object type is known, properties of that object can be used to rule out solutions where the geometry is inconsistent with objects of that type. For example, human hands have a certain range of sizes and expected eccentricities in various cross-sections, and such ranges can be used to filter the solutions in a particular slice. These constraints can be represented in any suitable format, e.g, a physical model (as described below), an ordered list of parameters based on such a model, etc.

In some embodiments, cross-slice correlations can also be used to filter (or further filter) the solutions obtained at block 612. For example, if the object is known to be a hand, constraints on the spatial relationship between various parts of the hand (e.g., fingers have a limited range of motion relative to each other and/or to the palm of the hand) as represented in a physical model or explicit set of constraint parameters can be used to constrain one slice based on results from other slices. For purposes of cross-slice correlations, it should be noted that, as a result of the way slices are defined, the various slices may be tilted relative to each other, e.g., as shown in FIG. 3B. Accordingly, each planar cross-section can be further characterized by an additional angle ø, which can be defined relative to a reference direction 310 as shown in FIG. 3B.

At block 616, it is determined whether a satisfactory solution has been found. Various criteria can be used to assess whether a solution is satisfactory. For instance, if a unique solution is found (after filtering), that solution can be accepted, in which case process 600 proceeds to block 620 (described below). If multiple solutions remain or if all solutions were rejected in the filtering at block 614, it may be desirable to retry the analysis. If so, process 600 can return to block 610, allowing a change in the assumption used in computing the parameters of the ellipse.

Retrying can be triggered under various conditions. For example, in some instances, the initial parameter assumption (e.g., a=a$_0$) may produce no solutions or only nonphysical solutions (e.g., object outside the cameras' field of view). In this case, the analysis can be retried with a different assumption. In one embodiment, a small constant (which can be positive or negative) is added to the initial assumed parameter value (e.g., a$_0$) and the new value is used to generate a new set of solutions. This can be repeated until an acceptable solution is found (or until the parameter value reaches a limit). An alternative approach is to keep the same assumption but to relax the constraint that the ellipse be tangent to all four lines, e.g., by allowing the ellipse to be nearly but not exactly tangent to one or more of the lines. (In some embodiments, this relaxed constraint can also be used in the initial pass through the analysis.)

It should be noted that in some embodiments, multiple elliptical cross-sections may be found in some or all of the slices. For example, in some planes, a complex object (e.g., a hand) may have a cross-section with multiple disjoint elements (e.g., in a plane that intersects the fingers). Ellipse-based reconstruction techniques as described herein can account for such complexity; examples are described below. Thus, it is generally not required that a single ellipse be found in a slice, and in some instances, solutions entailing multiple ellipses may be favored.

For a given slice, the analysis of FIG. 6B yields zero or more elliptical cross-sections. In some instances, even after filtering at block 616, there may still be two or more possible solutions. These ambiguities can be addressed in further processing as described below.

Referring again to FIG. 6A, the per-slice analysis of block 604 can be performed for any number of slices, and different slices can be analyzed in parallel or sequentially, depending on available processing resources. The result is a 3D model of the object, where the model is constructed by, in effect, stacking the slices. At block 620, cross-slice correlations are used to refine the model. For example, as noted above, in some instances, multiple solutions may have been found for a particular slice. It is likely that the "correct" solution (i.e., the ellipse that best corresponds to the actual position of the object) will correlate well with solutions in other slices, while any "spurious" solutions (i.e., ellipses that do not correspond to the actual position of the object) will not. Uncorrelated ellipses can be discarded. In some embodiments where slices are analyzed sequentially, block 620 can be performed iteratively as each slice is analyzed.

At block 622, the 3D model can be further refined, e.g., based on an identification of the type of object being modeled. In some embodiments, a library of object types can be provided (e.g., as object library 230 of FIG. 2). For each object type, the library can provide characteristic parameters for the object in a range of possible poses (e.g., in the case of a hand, the poses can include different finger positions, different orientations relative to the cameras, etc.). Based on these characteristic parameters, a reconstructed 3D model can be compared to various object types in the library. If a match is found, the matching object type is assigned to the model.

Once an object type is determined, the 3D model can be refined using constraints based on characteristics of the object type. For instance, a human hand would characteristically have five fingers (not six), and the fingers would be constrained in their positions and angles relative to each other and to a palm portion of the hand. Any ellipses in the model that are inconsistent with these constraints can be discarded. In some embodiments, block 622 can include recomputing all or portions of the per-slice analysis (block 604) and/or cross-slice correlation analysis (block 620) subject to the type-based constraints. In some instances, applying type-based constraints may cause deterioration in accuracy of reconstruction if the object is misidentified. (Whether this is a concern depends on implementation, and type-based constraints can be omitted if desired.)

In some embodiments, object library 230 can be dynamically and/or iteratively updated. For example, based on characteristic parameters, an object being modeled can be identified as a hand. As the motion of the hand is modeled across time, information from the model can be used to revise the characteristic parameters and/or define additional characteristic parameters, e.g., additional poses that a hand may present.

In some embodiments, refinement at block 622 can also include correlating results of analyzing images across time. It is contemplated that a series of images can be obtained as the object moves and/or articulates. Since the images are expected to include the same object, information about the object determined from one set of images at one time can be used to constrain the model of the object at a later time. (Temporal refinement can also be performed "backward" in time, with information from later images being used to refine analysis of images at earlier times.)

At block 624, a next set of images can be obtained, and process 600 can return to block 604 to analyze slices of the next set of images. In some embodiments, analysis of the next set of images can be informed by results of analyzing previous sets. For example, if an object type was determined, type-based constraints can be applied in the initial per-slice analysis, on the assumption that successive images are of the same object. In addition, images can be correlated across time, and these correlations can be used to further refine the model, e.g., by rejecting discontinuous jumps in the object's position or ellipses that appear at one time point but completely disappear at the next.

It will be appreciated that the motion capture process described herein is illustrative and that variations and modifications are possible. Steps described as sequential may be executed in parallel, order of steps may be varied, and steps may be modified, combined, added or omitted. Different mathematical formulations and/or solution procedures can be substituted for those shown herein. Various phases of the analysis can be iterated, as noted above, and the degree to which iterative improvement is used may be chosen based on a particular application of the technology. For example, if motion capture is being used to provide real-time interaction (e.g., to control a computer system), the data capture and analysis should be performed fast enough that the system response feels like real time to the user. Inaccuracies in the model can be tolerated as long as they do not adversely affect the interpretation or response to a user's motion. In other applications, e.g., where the motion capture data is to be used for rendering in the context of digital movie-making, an analysis with more iterations that produces a more refined (and accurate) model may be preferred. As noted above, an object being modeled can be a "complex" object and consequently may present multiple discrete ellipses in some cross-sections. For example, a hand has fingers, and a cross-section through the fingers may include as many as five discrete elements. The analysis techniques described above can be used to model complex objects.

Figure 11A:
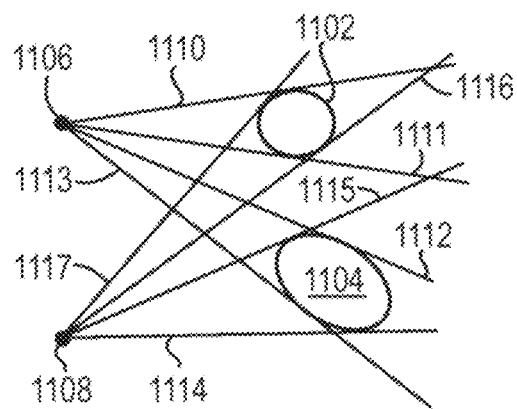
FIGS. 11A, 11B and 11C are top views illustrating instances of slices containing multiple disjoint cross-sections according to various embodiments of the present invention.
Figure 11B:
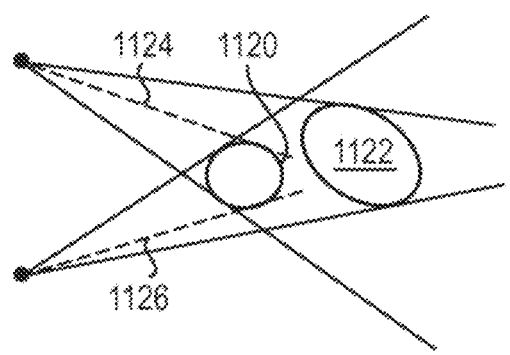
Figure 11C:
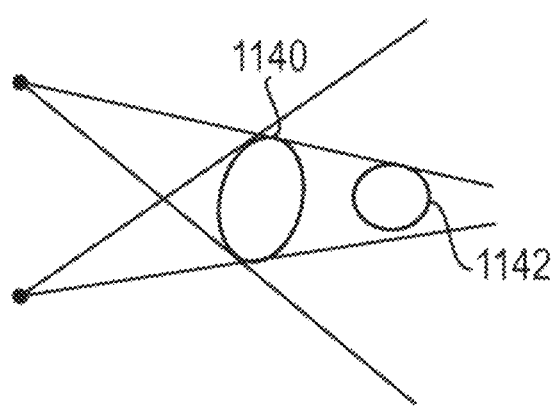

By way of example, FIGS. 11A-11C illustrate some cases of interest. In FIG. 11A, cross-sections 1102, 1104 would appear as distinct objects in images from both of vantage points 1106, 1108. In some embodiments, it is possible to distinguish object from background; for example, in an infrared image, a heat-producing object (e.g., living organisms) may appear bright against a dark background. Where object can be distinguished from background, tangent lines 1110 and 1111 can be identified as a pair of tangents associated with opposite edges of one apparent object while tangent lines 1112 and 1113 can be identified as a pair of tangents associated with opposite edges of another apparent object. Similarly, tangent lines 1114 and 1115, and tangent lines 1116 and 1117 can be paired. If it is known that vantage points 1106 and 1108 are on the same side of the object to be modeled, it is possible to infer that tangent pairs 1110, 1111 and 1116, 1117 should be associated with the same apparent object, and similarly for tangent pairs 1112, 1113 and 1114, 1115. This reduces the problem to two instances of the ellipse-fitting process described above. If less information is available, an optimum solution can be determined by iteratively trying different possible assignments of the tangents in the slice in question, rejecting non-physical solutions, and cross-correlating results from other slices to determine the most likely set of ellipses.

In FIG. 11B, ellipse 1120 partially occludes ellipse 1122 from both vantage points. In some embodiments, it may or may not be possible to detect the "occlusion" edges 1124, 1126. If edges 1124 and 1126 are not detected, the image appears as a single object and is reconstructed as a single elliptical cross-section. In this instance, information from other slices or temporal correlation across images may reveal the error. If occlusion edges 1124 and/or 1126 are visible, it may be apparent that there are multiple objects (or that the object has a complex shape) but it may not be apparent which object or object portion is in front. In this case, it is possible to compute multiple alternative solutions, and the optimum solution may be ambiguous. Spatial correlations across slices, temporal correlations across image sets, and/or physical constraints based on object type can be used to resolve the ambiguity.

In FIG. 11C, ellipse 1140 fully occludes ellipse 1142. In this case, the analysis described above would not show ellipse 1142 in this particular slice. However, spatial correlations across slices, temporal correlations across image sets, and/or physical constraints based on object type can be used to infer the presence of ellipse 1142, and its position can be further constrained by the fact that it is apparently occluded. In some embodiments, multiple discrete cross-sections (e.g., in any of FIGS. 11A-11C) can also be resolved using successive image sets across time. For example, the four-tangent slices for successive images can be aligned and used to define a slice with 5-8 tangents. This slice can be analyzed using techniques described below.

In one embodiment of the present invention, a motion capture system can be used to detect the 3D position and movement of a human hand. In this embodiment, two cameras are arranged as shown in FIG. 1, with a spacing of about 1.5 cm between them. Each camera is an infrared camera with an image rate of about 60 frames per second and a resolution of 640×480 pixels per frame. An infrared light source (e.g., an IR light-emitting diode) that approximates a point light source is placed between the cameras to create a strong contrast between the object of interest (in this case, a hand) and background. The falloff of light with distance creates a strong contrast if the object is a few inches away from the light source while the background is several feet away.

The image is analyzed using contrast between adjacent pixels to detect edges of the object. Bright pixels (detected illumination above a threshold) are assumed to be part of the object while dark pixels (detected illumination below a threshold) are assumed to be part of the background. Edge detection may take approximately 2 ms with conventional processing capability. The edges and the known camera positions are used to define tangent lines in each of 480 slices (one slice per row of pixels), and ellipses are determined from the tangents using the analytical technique described above with reference to FIGS. 6A and 6B. In a typical case of modeling a hand, roughly 800-1200 ellipses are generated from a single pair of image frames (the number depends on the orientation and shape of the hand) within, in various embodiments, about 6 ms. The error in modeling finger position in one embodiment is less than 0.1 mm.

Figure 12:
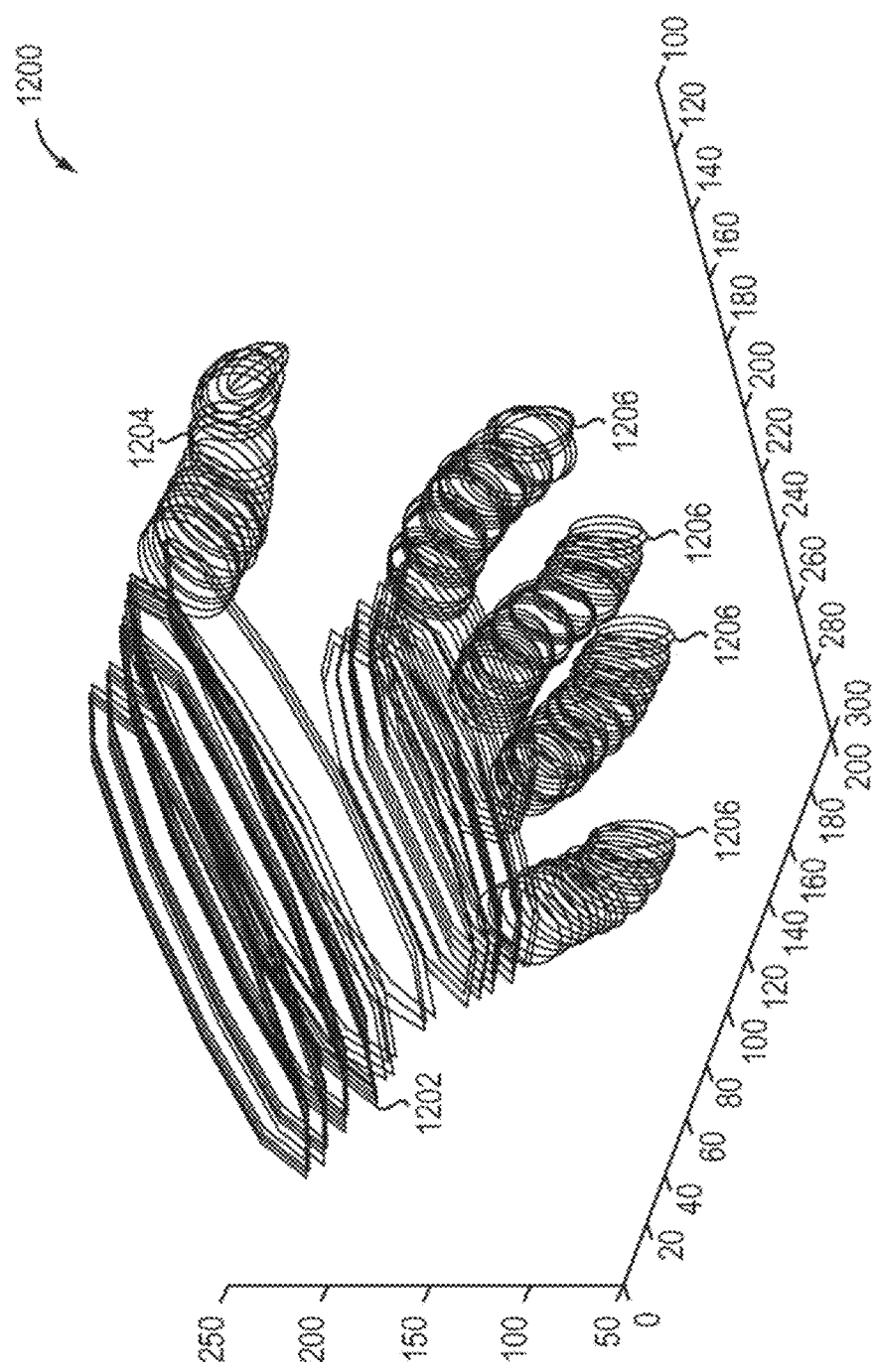
FIG. 12 graphically illustrates a model of a hand that can be generated using a motion capture system according to an embodiment of the present invention.

FIG. 12 illustrates a model 1200 of a hand that can be generated using the system just described. As can be seen, the model does not have the exact shape of a hand, but a palm 1202, thumb 1204 and four fingers 1206 can be clearly recognized. Such models can be useful as the basis for constructing more realistic models. For example, a skeleton model for a hand can be defined, and the positions of various joints in the skeleton model can be determined by reference to model 1200. Using the skeleton model, a more realistic image of a hand can be rendered. Alternatively, a more realistic model may not be needed. For example, model 1200 accurately indicates the position of thumb 1204 and fingers 1206, and a sequence of models 1200 captured across time will indicate movement of these digits. Thus, gestures can be recognized directly from model 1200. The point is that ellipses identified and tracked as described above can be used to drive visual representations of the object tracked by application to a physical model of the object. The model may be selected based on a desired degree of realism, the response time desired (or the latency that can be tolerated), and available computational resources.

It will be appreciated that this example system is illustrative and that variations and modifications are possible. Different types and arrangements of cameras can be used, and appropriate image analysis techniques can be used to distinguish object from background and thereby determine a silhouette (or a set of edge locations for the object) that can in turn be used to define tangent lines to the object in various 2D slices as described above. Given four tangent lines to an object, where the tangents are associated with at least two vantage points, an elliptical cross-section can be determined; for this purpose it does not matter how the tangent lines are determined. Thus, a variety of imaging systems and techniques can be used to capture images of an object that can be used for edge detection. In some cases, more than four tangents can be determined in a given slice. For example, more than two vantage points can be provided.

Figure 13:
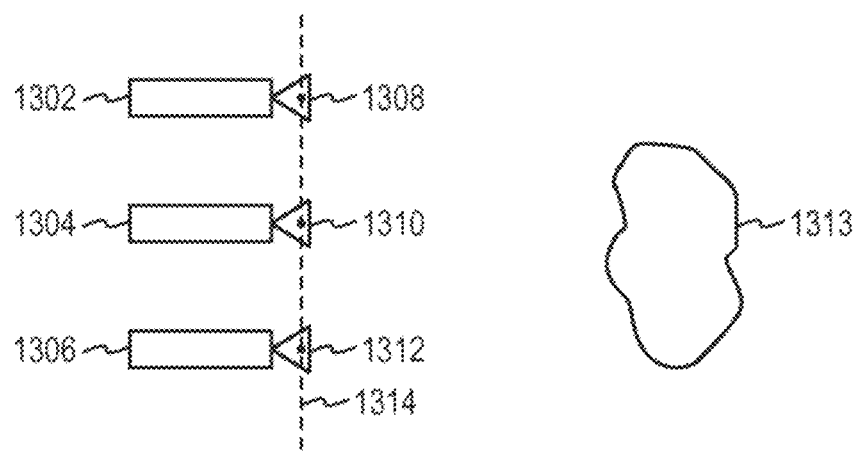
FIG. 13 is a simplified system diagram for a motion-capture system with three cameras according to an embodiment of the present invention.
Figure 14:
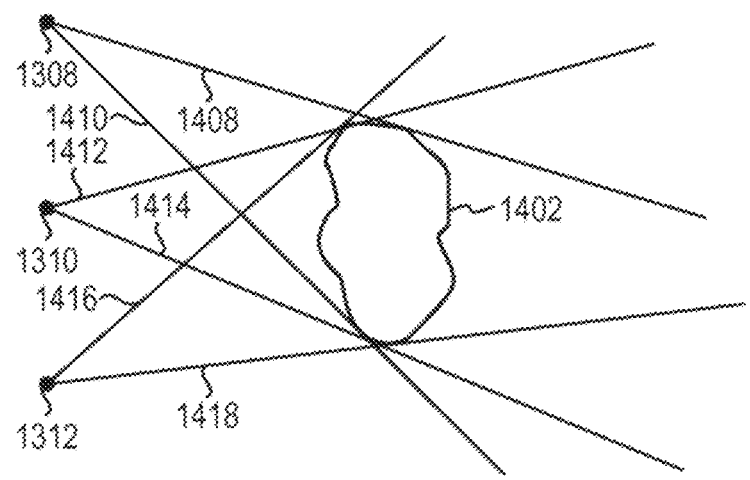
FIG. 14 illustrates a cross-section of an object as seen from three vantage points in the system of FIG. 13.

In one alternative embodiment, three cameras can be used to capture images of an object. FIG. 13 is a simplified system diagram for a system 1300 with three cameras 1302, 1304, 1306 according to an embodiment of the present invention. Each camera 1302, 1304, 1306 provides a vantage point 1308, 1310, 1312 and is oriented toward an object of interest 1313. In this embodiment, cameras 1302, 1304, 1306 are arranged such that vantage points 1308, 1310, 1312 lie in a single line 1314 in 3D space. Two-dimensional slices can be defined as described above, except that all three vantage points 1308, 1310, 1312 are included in each slice. The optical axes of cameras 1302, 1304, 1306 can be but need not be aligned, as long as the locations of vantage points 1308, 1310, 1312 are known. With three cameras, six tangents to an object can be available in a single slice. FIG. 14 illustrates a cross-section 1402 of an object as seen from vantage points 1308, 1310, 1312. Lines 1408, 1410, 1412, 1414, 1416, 1418 are tangent lines to cross-section 1402 from vantage points 1308, 1310, 1312, respectively.

Figure 15:
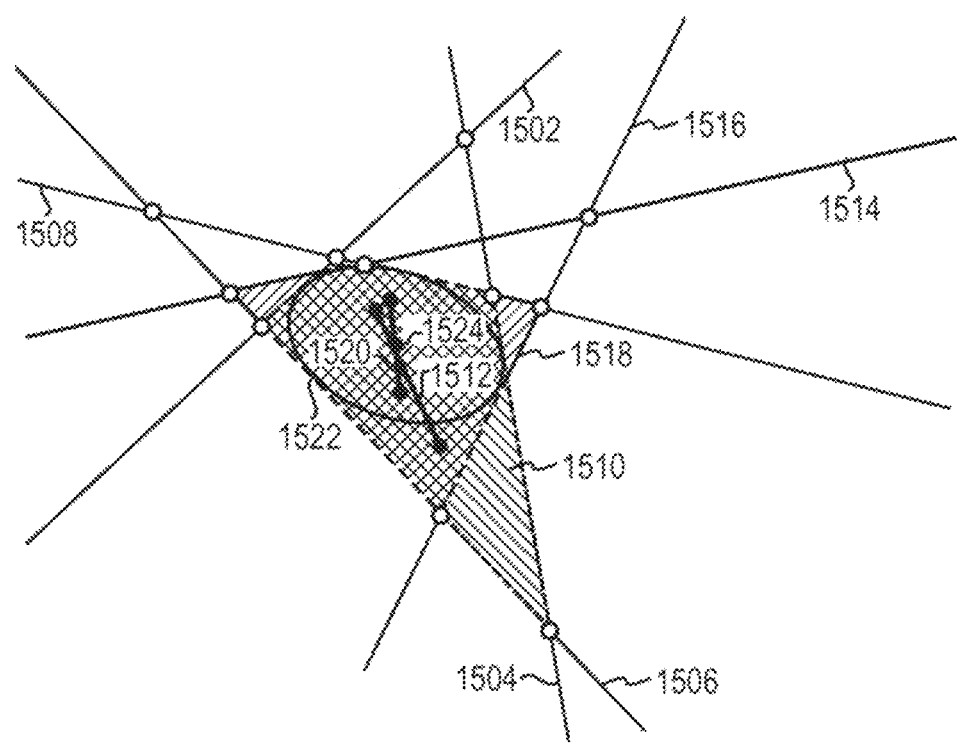
FIG. 15 graphically illustrates a technique that can be used to find an ellipse from at least five tangents according to an embodiment of the present invention.

For any slice with five or more tangents, the parameters of an ellipse are fully determined, and a variety of techniques can be used to fit an elliptical cross-section to the tangent lines. FIG. 15 illustrates one technique, relying on the "centerline" concept illustrated above in FIG. 9. From a first set of four tangents 1502, 1504, 1506, 1508 associated with a first pair of vantage points, a first intersection region 1510 and corresponding centerline 1512 can be determined. From a second set of four tangents 1504, 1506, 1514, 1516 associated with a second pair of vantage points, a second intersection region 1518 and corresponding centerline 1520 can be determined. The ellipse of interest 1522 should be inscribed in both intersection regions. The center of ellipse 1522 is therefore the intersection point 1524 of centerlines 1512 and 1520. In this example, one of the vantage points (and the corresponding two tangents 1504, 1506) are used for both sets of tangents. Given more than three vantage points, the two sets of tangents could be disjoint if desired.

Where more than five tangent points (or other points on the object's surface) are available, the elliptical cross-section is mathematically overdetermined. The extra information can be used to refine the elliptical parameters, e.g., using statistical criteria for a best fit. In other embodiments, the extra information can be used to determine an ellipse for every combination of five tangents, then combine the elliptical contours in a piecewise fashion. Alternatively, the extra information can be used to weaken the assumption that the cross-section is an ellipse and allow for a more detailed contour. For example, a cubic closed curve can be fit to five or more tangents.

In some embodiments, data from three or more vantage points is used where available, and four-tangent techniques (e.g., as described above) can be used for areas that are within the field of view of only two of the vantage points, thereby expanding the spatial range of a motion-capture system.

While thus far the invention has been described with respect to specific embodiments, one skilled in the art will recognize that numerous modifications are possible. The techniques described above can be used to reconstruct objects from as few as four tangent lines in a slice, where the tangent lines are defined between edges of a projection of the object onto a plane and two different vantage points. Thus, for purposes of the analysis techniques described herein, the edges of an object in an image are of primary significance. Any image or imaging system that supports determining locations of edges of an object in an image plane can therefore be used to obtain data for the analysis described herein.

For instance, in embodiments described above, the object is projected onto an image plane using two different cameras to provide the two different vantage points, and the edge points are defined in the image plane of each camera. However, those skilled in the art with access to the present disclosure will appreciate that it may be possible to use a single camera to capture motion and/or determine the shape and position of the object in 3D space.

Additionally, those skilled in the art with access to the present disclosure will appreciate that cameras are not the only tool capable of projecting an object onto an imaging surface. For example, a light source can create a shadow of an object on a target surface, and the shadow—captured as an image of the target surface—can provide a projection of the object that suffices for detecting edges and defining tangent lines. The light source can produce light in any visible or non-visible portion of the electromagnetic spectrum. Any frequency (or range of frequencies) can be used, provided that the object of interest is opaque to such frequencies while the ambient environment in which the object moves is not. The light sources used should be bright enough to cast distinct shadows on the target surface. Point-like light sources provide sharper edges than diffuse light sources, but any type of light source can be used.

Figure 16:
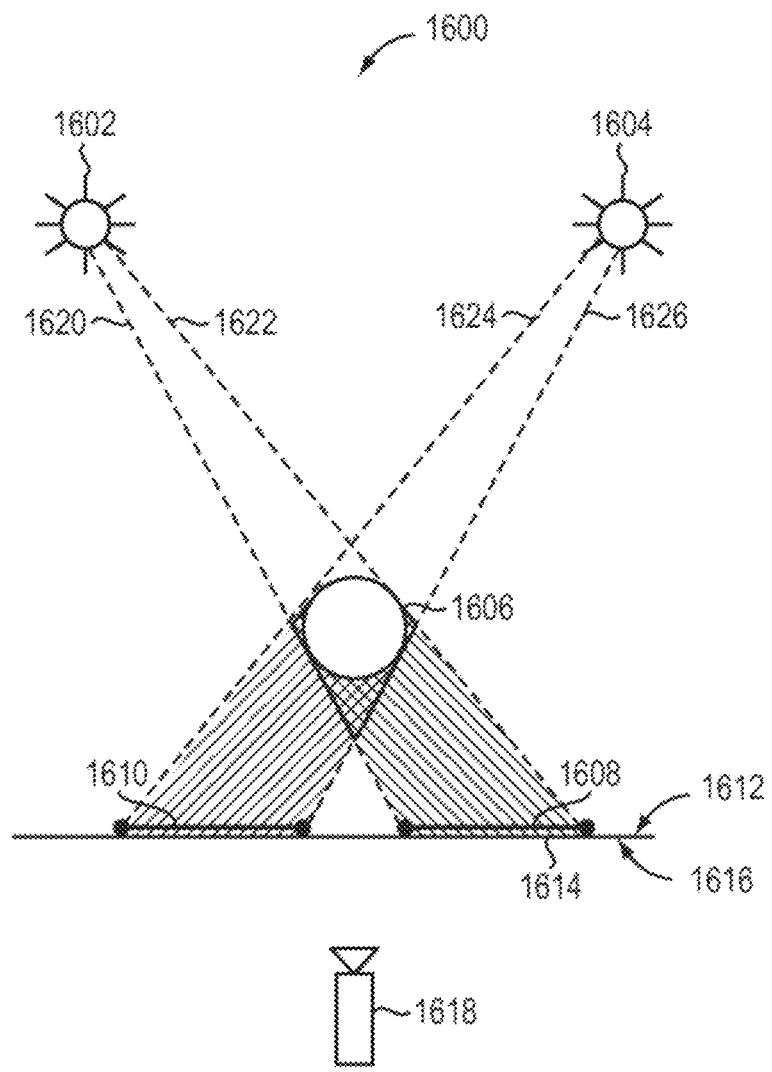
FIG. 16 schematically illustrates a system for capturing shadows of an object according to an embodiment of the present invention.

In one such embodiment, a single camera is used to capture images of shadows cast by multiple light sources. FIG. 16 illustrates a system 1600 for capturing shadows of an object according to an embodiment of the present invention. Light sources 1602 and 1604 illuminate an object 1606, casting shadows 1608, 1610 onto a front side 1612 of a surface 1614. Surface 1614 can be translucent so that the shadows are also visible on its back side 1616. A camera 1618 can be oriented toward back side 1616 as shown and can capture images of shadows 1608, 1610. With this arrangement, object 1606 does not occlude the shadows captured by camera 1618. Light sources 1602 and 1604 define two vantage points, from which tangent lines 1620, 1622, 1624, 1626 can be determined based on the edges of shadows 1608, 1610. These four tangents can be analyzed using techniques described above.

In an embodiment such as system 1600 of FIG. 16, shadows created by different light sources may partially overlap, depending on where the object is placed relative to the light source. In such a case, an image may have shadows with penumbra regions (where only one light source is contributing to the shadow) and an umbra region (where the shadows from both light sources overlap). Detecting edges can include detecting the transition from penumbra to umbra region (or vice versa) and inferring a shadow edge at that location. Since an umbra region will be darker than a penumbra region; contrast-based analysis can be used to detect these transitions.

Figure 17:
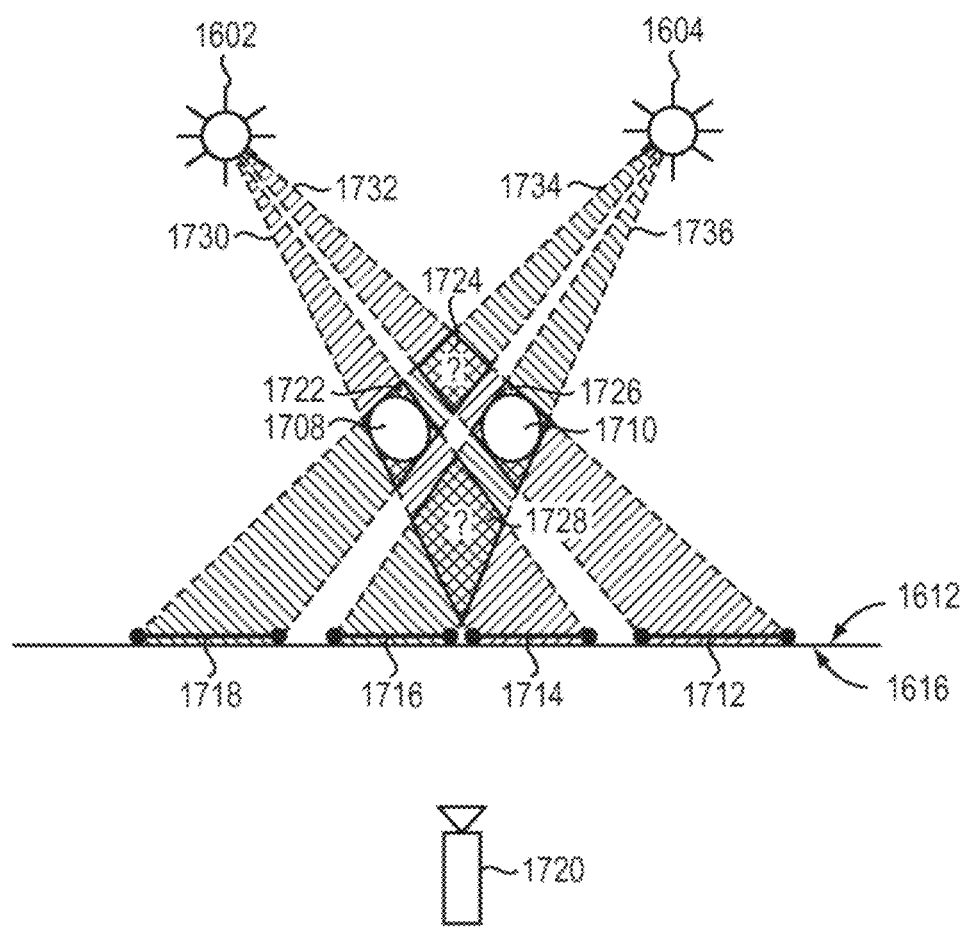
FIG. 17 schematically illustrates an ambiguity that can occur in the system of FIG. 16.

Certain physical or object configurations may present ambiguities that are resolved in accordance with various embodiments we as now discussed. Referring to FIG. 17, when two objects 1708, 1710 are present, the camera 1720 may detect four shadows 1712, 1714, 1716, 1718 and the tangent lines may create four intersection regions 1722, 1724, 1726, 1728 that all lie within the shadow regions 1730, 1732, 1734, 1736. Because it is difficult to determine, from a single slice of the shadow image, which of these intersection regions contain portions of the object, an analysis of whether the intersection regions 1722, 1724, 1726, 1728 are occupied by the objects may be ambiguous. For example, shadows 1712, 1714, 1716, 1718 that are generated when intersection regions 1722 and 1726 are occupied are the same as those generated when regions 1724 and 1728 are occupied, or when all four intersection regions 1722, 1724, 1726, 1728 are occupied. In one embodiment, correlations across slices are used to resolve the ambiguity in interpreting the intersection regions (or "visual hulls") 1722, 1724, 1726, 1728.

Figure 18:
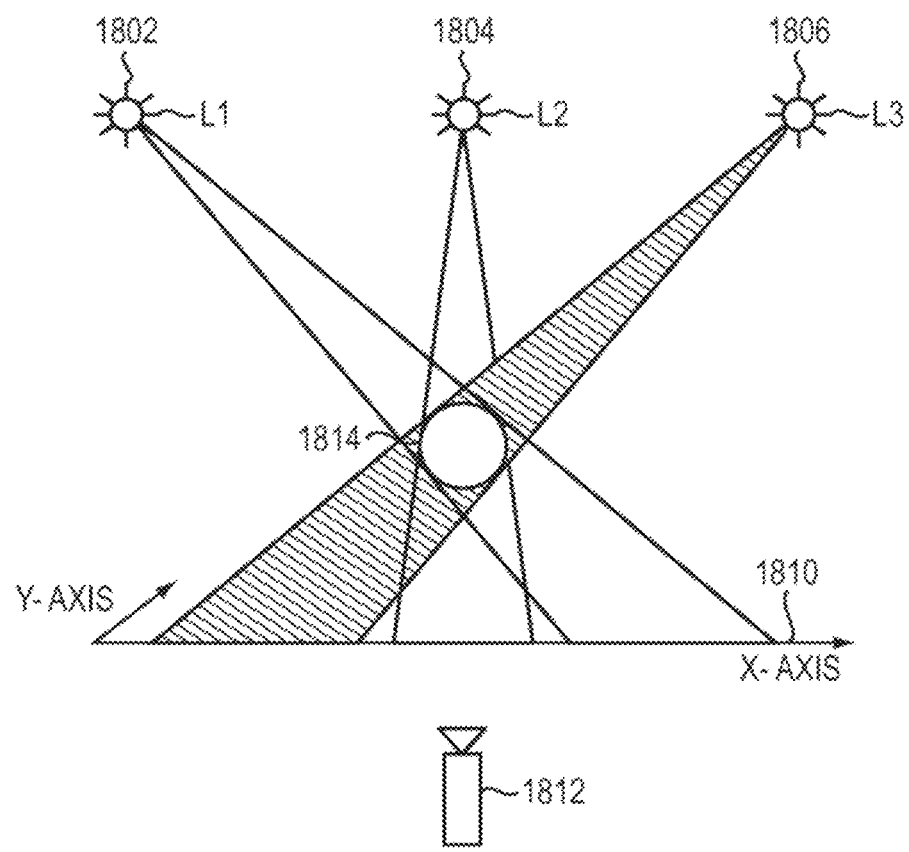
FIG. 18 schematically illustrates another system for capturing shadows of an object according to another embodiment of the present invention.

In various embodiments, referring to FIG. 18, a system 1800 incorporates a large number of light sources (i.e., more than two light sources) to resolve the ambiguity of the intersection regions when there are multiple objects casting shadows. For example, the system 1800 includes three light sources 1802, 1804, 1806 to cast light onto a translucent surface 1810 and a camera 1812 positioned on the opposite side of surface 1810 to avoid occluding the shadows cast by an object 1814. As shown in FIG. 18, because utilization of three light sources provides five or more tangents for one or more objects 1814 in a slice, the ellipse-fitting techniques described above may be used to determine the cross-sections of the objects. A collection of the cross-sections of the objects in 2D slices may then determine the locations and/or movement of the objects.

If multiple objects, however, are located in close proximity (e.g., the fingers of a hand), utilization of additional light sources may reduce the sizes of the various intersection regions as well as increase the total number of intersection regions. If the number of light sources is much greater than the number of the proximal objects, the intersection regions may be too small to be analyzed based on a known or assumed size scale of the object. Additionally, the increased number of intersection regions may result in more ambiguity in distinguishing intersection regions that contain objects from intersection regions that do not contain objects (i.e., "blind spots"). In various embodiments, whether an intersection region contains an object is determined based on the properties of a collection of intersection points therein. As described in greater detail below, an intersection point is defined by at least two shadow lines, each connecting a shadow point of the shadow and a light source. If the intersection points in an intersection region satisfy certain criteria, the intersection region is considered to have the objects therein. A collection of the intersection regions may then be utilized to determine the shape and movement of the objects.

Figure 19:
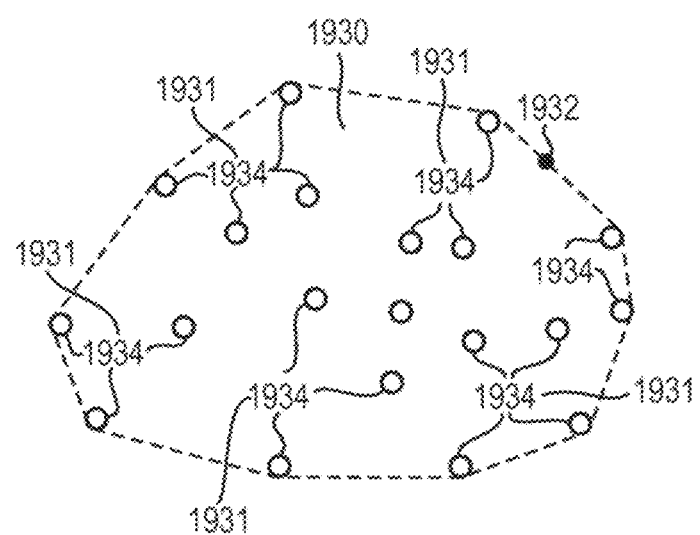
FIG. 19 graphically depicts a collection of the intersection regions defined by a virtual rubber band stretched around multiple intersection regions in accordance with an embodiment of the invention.

Referring to FIG. 19, a collection of the intersection regions (a visual hull) 1930 is defined by a virtual rubber band 1932 stretched around multiple intersection regions 1931 (or "convex hulls"); each intersection region 1931 is defined by a smallest set of intersection points 1934. When there are multiple intersection regions 1931, distinguishing each intersection region 1931 from a collection of intersection points 1934 may be difficult. In some embodiments, referring to FIG. 20, a simple visual hull is first constructed by a setup of two lights 2002, 2004 (here denoted Ln, with n={1, 2} to permit further generalization to greater numbers of light sources, shadows, shadow regions, points, and visual hulls), each casting one shadow 2006A, 2006B, respectively. The light source $L_1$ and shadow 2006A define a shadow region, $R_{1,1}$; similarly, light source $L_2$ and the shadow 2006B define a shadow region, $R_{2,1}$; in general, the shadow region is denoted as, $R_{u,v}$, where u is the number of the corresponding light source and v is a number that denotes a left to right ordering in a scene within the set of all shadow regions from the light source u. Boundaries of the shadows (or "shadow points") lie on an x axis and are denoted by $S_{u,v}$. The shadow points and each light source may then create shadow lines 2008, 2010, 2012, 2014; the shadow lines are referenced by the two connecting points; for example, $\overline{L_1 S_{1,2}}$, (abbreviated $\overline{S_{1,2}}$, where the first subscript also refers to the light number). The convex hull 2030 (or visual hull here since there is only one intersection region 2028) may then be defined by the four intersection points 2034 in the example of FIG. 20. In one embodiment, the intersection points 2034 are determined based on the intersections of every pair of shadow lines, for example, $\overline{S_{1,1}}$, $\overline{S_{1,2}}$, $\overline{S_{2,1}}$, and $\overline{S_{2,2}}$. Because pairs of shadow lines from the same light source $L_1$ or $L_2$ do not intersect, the intersection of the pairs of lines from the same light source may then be neglected.

Figure 21A:
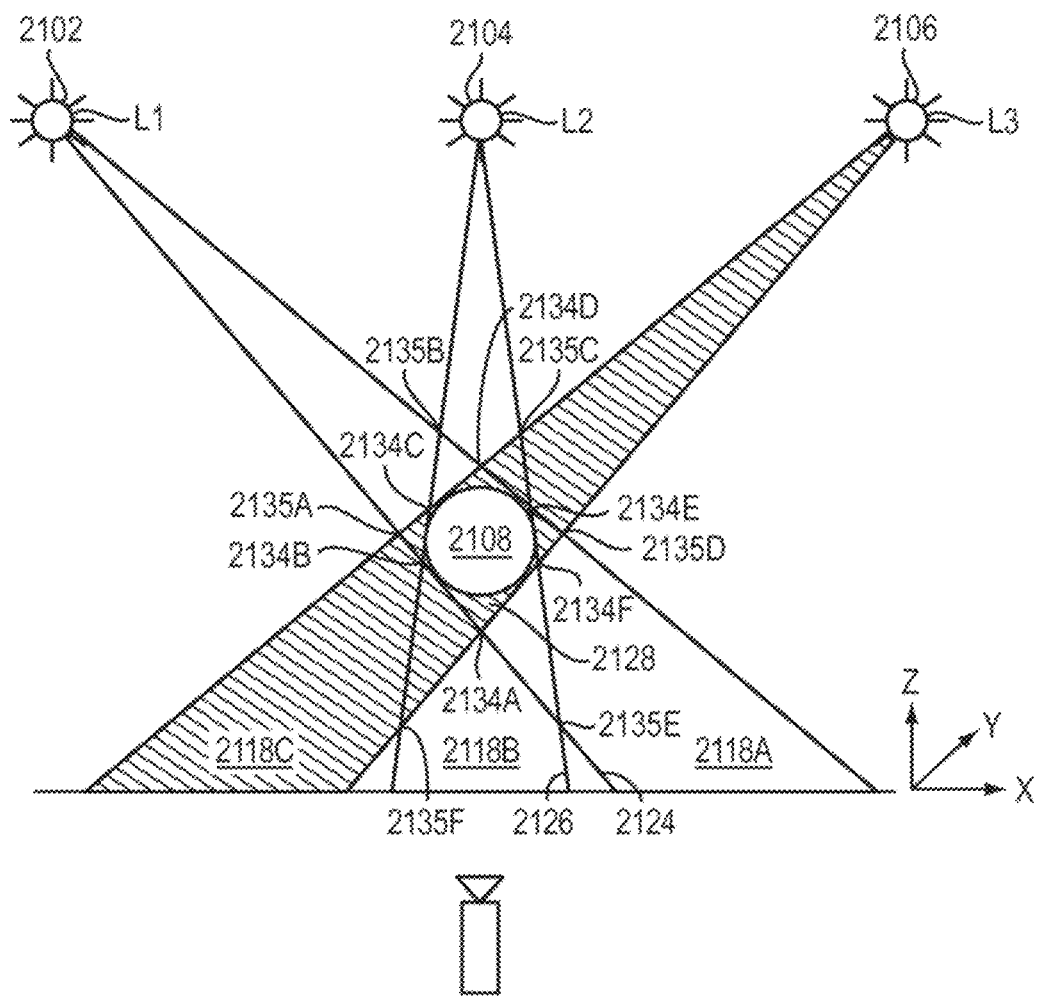
FIGS. 21A, 21B and 21C schematically depict determinations of true intersection points in accordance with various embodiments of the invention.

When there are more than two light sources, determining all shadow line intersections no longer suffices to find intersection points that lie on the intersection region 2028. Referring to FIG. 21A, utilization of three light sources 2102, 2104, 2106, may result in "true" intersection points 2134A, 2134B, 2134C, 2134D, 2134E, 2134F that form the intersection region 2128 occupied by the object 2108 and "false" intersection points 2135A, 2135B, 2135C, 2135D, 2135E, 2135F that clearly do not form the intersection region 2128. For example, the false intersection point 2135E created by a left shadow line 2124 of the shadow region 2118A and a right shadow line 2126 of the shadow region 2118B is a false intersection point because it does not lie inside the intersection region 2128. Because the intersection region 2128 is an intersection of the shadow regions 2118A, 2118B, 2118C created by the object 2108 and the light sources 2102, 2104, 2106, the number of shadow regions in which each "true" intersection point lies is equal to the number of the light sources (i.e., three in FIG. 21A). "False" intersection points, by contrast, lie outside the intersection region 2128 even though they may lie inside an intersection region that includes fewer number of shadow regions compared to the total number of light sources. In one embodiment, whether an intersection point is "true" or "false" is determined based on the number of shadow regions included in the intersection region in which the intersection point lies. For example, in the presence of three light sources in FIG. 21A, the intersection point 2134A is a true intersection point because it lies inside three shadow regions 2118A, 2118B, 2118C; whereas the intersection point 2135F is a false intersection point because it lies inside only two shadow regions 2118B, 2118C.

Because the intersection regions are defined by a collection of intersection points, excessive computational effort may be required to determine whether an intersection point is contained by a correct number of regions (i.e., the number of the light sources). In some embodiments, this computational complexity is reduced by assuming that each intersection point is not "false" and then determining whether the results are consistent with all of the shadows captured by the camera. These configurations project each intersection point I=[$I_x,I_y$] onto the x axis through a ray directed from each light source L=[$L_x,L_y$] that is not involved in the original intersection determination. The solutions for these projections are given by $$\left[ \frac{L_y P_x - L_x P_y}{L_y - P_y}, 0 \right].$$

Figure 21B:
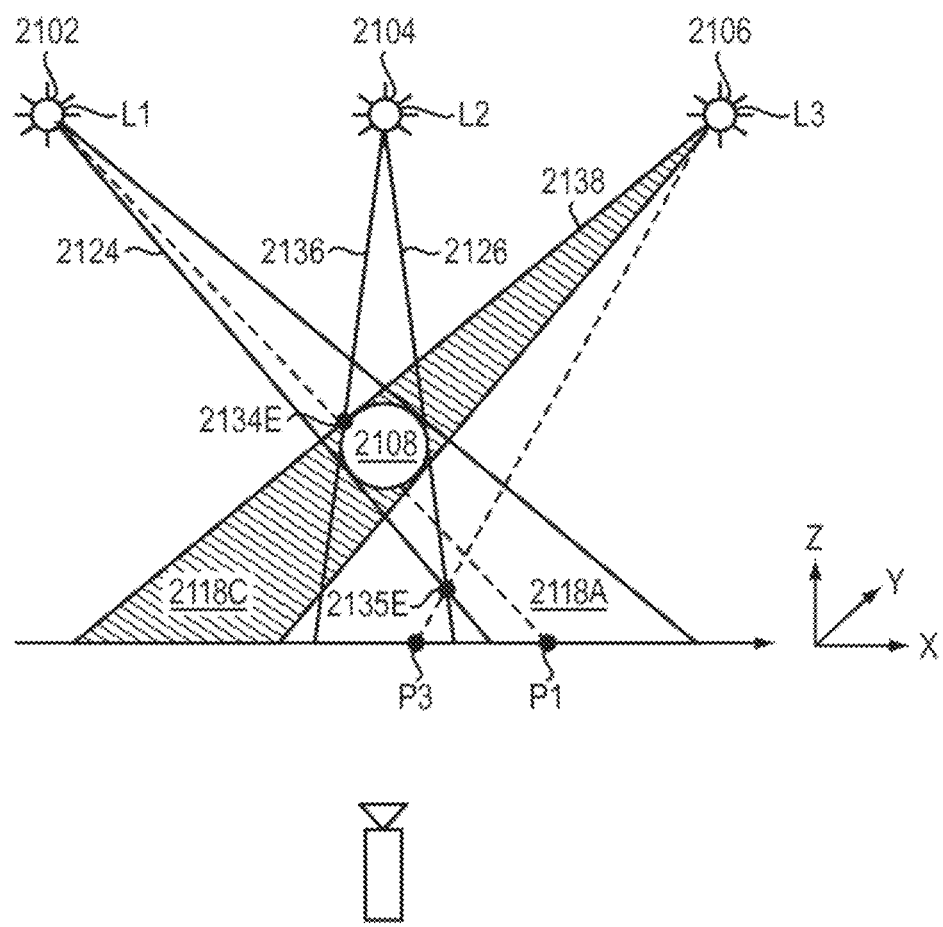

If a projection point on the x axis lies inside a shadow region from the testing light source, it is likely that the projected intersection point is a true intersection point. For example, referring to FIG. 21B, the intersection point 2135E is determined by the shadow lines 2124 and 2126 created by the light sources 2102 and 2106. Projecting the intersection point 2135E onto the x axis using the light source 2106, which is not involved in determining the intersection point 2135E, creates a projection point $P_3$. Because the projection point $P_3$ does not lie inside the shadow region 2118C created by the light source 2106 and the object 2108, the intersection point 2135E is considered to be a false intersection point; whereas the intersection point 2134E is a true intersection point because the projection point $P_1$ thereof lies within the shadow region 2118A. As a result, for every possible intersection point, an additional N−2 projections must be determined for the N−2 light sources that are not involved in determining the position of the intersection point (where N is the total number of light sources in the system). In other words, a projection check must be made for every light source other than the original two that are used to determine the tested intersection point. Because determining whether the intersection point is true or false based on the projections is simpler than checking the number of shadow regions in which each intersection point lies, the required computational requirements and processing time may be significantly reduced.

Figure 21C:
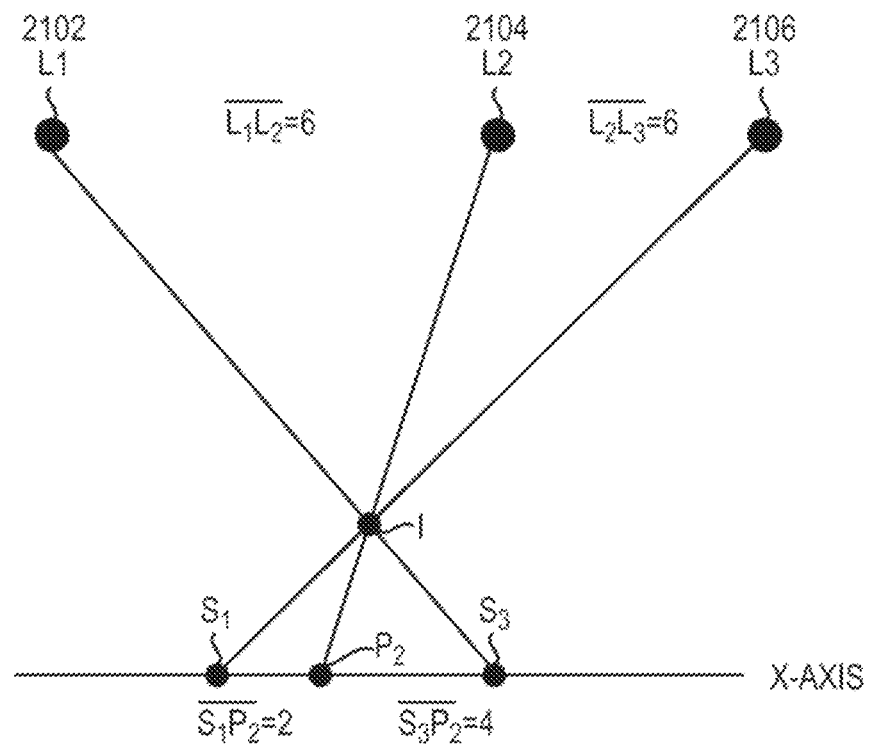

If, however, a large quantity of light sources is utilized in the system, the overall process may still be time-consuming. In various embodiments, the light sources $L_1$, $L_2$, and $L_3$ are placed in a line parallel to the x axis, the location of the projection points can then be determined without finding the location of the intersection point for every pair of shadow lines. Accordingly, whether the intersection point 2134 is a true or false point may be determined without finding or locating the position thereof, this further reduces the processing time. For example, with reference to FIG. 21C, assuming that the shadow points $S_1$ and $S_3$ are either known or have been determined, whether the intersection point I of the shadow lines $\overline{L_1 S_3}$ and $\overline{L_3 S_1}$ is true or false may be determined by the position of the projection point $P_2$ created by the light source $L_2$. The distance between the projection point $P_2$ created by the light source $L_2$ and the shadow point $S_1$ is given as:

$$\overline{S_1 P_2} = \overline{S_1 S_3} \left[ \frac{L_2 L_3}{L_1 L_3} \right] \quad \text{(Eq. 1)}$$

Thus, the location of any one of the projection points projected from the intersection point, I, and light sources may be determined based on the other two shadow points and the distance ratios associated with light sources $L_1$, $L_2$ and $L_3$. Because the ratio of the distances between the light sources is predetermined, the complexity in determining the projection point $P_2$ is reduced to little more than calculating distances between the shadow points and multiplying these distances by the predetermined ratio. If the distance between the projection point $P_2$ and the shadow point $S_1$ is larger than the size of the shadow, i.e., $\overline{S_1 S_3}$, that is captured by the camera, the intersection point, I, is a false point. If, on the other hand, the distance between the projection points $S_2$ and $S_1$ is smaller than the size of the shadow, the intersection point I is likely a true point. Although the location of the intersection point, I, may still be determined based on the shadow lines $\overline{L_1 S_3}$ and $\overline{L_3 S_1}$, this determination may be skipped during the process. Accordingly, by aligning the light sources in a line, the false intersection points can be quickly determined without performing the complex computations, thereby saving a large amount of processing time and power.

More generally, when there are N light sources, each denoted as $L_i$ ($1 \leq i \leq N$), arranged on a line parallel to the x axis and each light source possesses a set of $S_i$ shadow points (where i is the light number), a total number of M intersection calculations for all possible intersection pairs is given as:

$$M = \sum_{i=1}^{N-1} S_i \left( \sum_{k=i+1}^{N} S_k \right). \quad \text{(Eq. 2)}$$

For example, if there are N light sources, each casting n shadows, the total number of intersection calculations M may then be given as $$M = n^2 N(N-1). \quad \text{(Eq. 3)}$$

Because each of these intersection calculations involves multiple operations (e.g., addition and multiplication), the total number of operations, $T_o$, may be given as $$T_o = 2n^2 N(2N+1)(N-1). \quad \text{(Eq. 4)}$$

Figure 20:
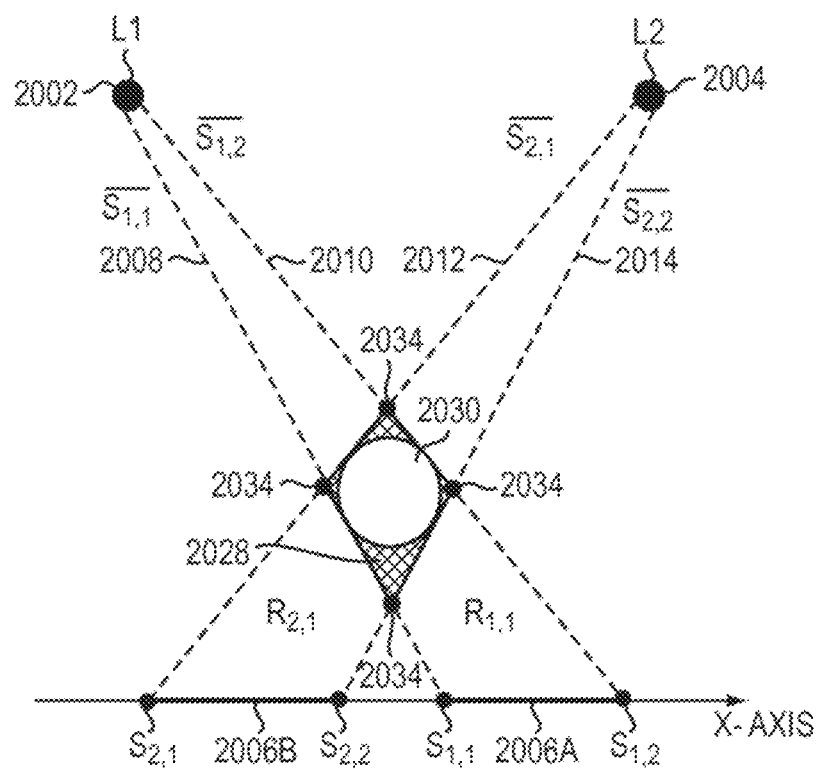
FIG. 20 schematically illustrates a simple intersection region constructed using two light sources in accordance with an embodiment of the invention.

For example, a total number of operations $T_o=2(1)^2 3(2 \cdot 3+1)(3-1)=84$ is required to determine the simplest visual hull 2028 shown in FIG. 20. In one embodiment, there are, for example, 12 light sources (i.e., N=12), each casting 10 shadows (i.e., n=10); the number of required intersection calculations for this scenario is M=13,200, setting the number of total operations to be $T_o$=660,000. Again, this requires a significant amount of processing time. In some embodiments, the distance ratios between light sources are predetermined, and as a result, only one operation (i.e., multiplication) is needed to determine which pairs of shadow points produce true intersection points; this reduces the number of total operations to 13,200.

The computational load required to find the visual hull depends on the quantity of the true intersection points, which may not be uniquely determined by the number of shadows. Suppose, for example, that there are N light sources and each object is a circle that casts one shadow per light; this results in N intersection regions (or 6N intersection points) per object. Because there are n objects, the resulting number of intersection points that need to be checked is $6Nn^2$ (i.e., roughly 6,000 for 10 objects cast by 12 light sources). As described above, the number of operations required for the projection check is 13,200; accordingly, a total number of operations 19,200 is necessary to determine the visual hull formed by the true intersection points. This is a 34-fold improvement in determining the solution for a single 2D scene compared to the previous estimate of 660,000 operations. The number of reduced operations may be given as:

$$T_P = n^2 N(N-1) + 6Nn^2 \quad (Eq. 5)$$

The ratio of the required operations to the reduced operations may then be expressed as:

$$\frac{T_o}{T_p} = \frac{2n(2N+1)(N-1)}{nN - n + 6n} \quad (Eq. 6)$$

Based on Eq. 6, if the light sources lie along a line or lines parallel to the x axis, the improvement is around an order of magnitude for a small number of lights, whereas the improvement is nearly two orders of magnitude for a larger number of lights.

If the objects are reconstructed in 3D space and/or a fast real-time refresh rate (e.g., 30 frames per second) is used by the camera, the computational load may be increased by several orders of magnitude due to the additional complexity. In some embodiments, the visual hull is split into a number of small intersection regions that can generate at least a portion of the shadows in the scene; the smallest cardinality of the set of small intersection regions is defined as a "minimal solution." In one embodiment, the number of the small intersection regions in the minimal solution is equal to the largest number of shadows generated by any single light source. The computational complexity of obtaining the visual hull may significantly be reduced by determining each of the small visual hulls prior to assembling them together into the visual hull.

Figure 22:
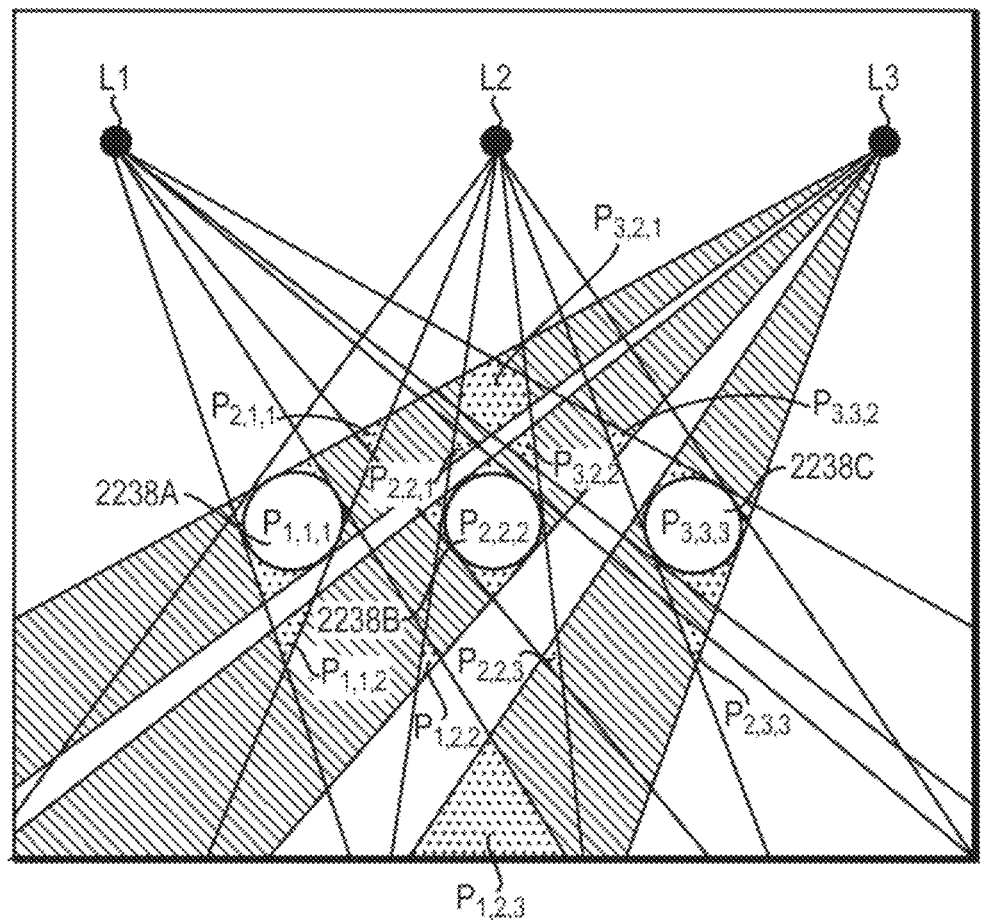
FIG. 22 schematically depicts an intersection region uniquely identified using a group of the intersection points.

Referring again to FIG. 19, the intersection points 1934 may form an amorphous cloud that does not imply particular regions. In various embodiments, this cloud is first split into a number of sets, each set determining an associated convex hull 1931. As further described below, in one embodiment, a measure is utilized to determine the intersection region to which each intersection point belongs. The determined intersection region may then be assembled into an exact visual hull. In one implementation, the trivial case of a visual hull containing only one intersection region is ignored. In some embodiments, every intersection region p is assigned an N-dimensional subscript, where N is the number of light sources in the scene under consideration. The nth entry for this subscript of the intersection region p is defined as the value v of the uth subscript (where u=n) for each shadow region $R_{u,v}$ of which the intersection region is a subset; every intersection region thus has a unique identifier for grouping the intersection points, as shown in FIG. 22. Because two of the subscript entries for an intersection point can be determined directly from the two shadow lines, the resulting intersection point thereof is in the two shadow regions in which the shadow lines are located. For the rest of the entries, the locations of the projections of the intersection points may be recorded during the determination of true and false intersection points. Complete knowledge of the particular intersection regions for each intersection point may thus be determined.

Once the distinct intersection regions have been determined, the smallest subset of intersection regions that can generate all of the final shadows may then be found. FIG. 22 depicts intersection regions $\rho_{1,1,1}$, $\rho_{2,2,2}$, $\rho_{3,3,3}$, resulting from casting light from three light sources onto three objects 2238A, 2238B, and 2238C. Because the greatest number of shadows cast by any particular light source in this case is three and the number of intersection regions in the minimal solution is equal to the largest number of shadows generated by any single light source, every group that includes three intersection regions in the scene may be tested. If a group generates a complete set of shadows captured by the camera, this group is the minimum solution. The number of trios to test is equal to the binomial coefficient $$C_u^j = \binom{j}{u} = \frac{j!}{u!(j-u)!},$$

where j is the total number of intersection regions. For example, there are $C_3^{13}=286$ combinations in FIG. 22. The likelihood that a trio having larger intersection regions can generate all of the captured shadows is higher than for a trio having smaller intersection regions; additionally, larger intersection regions usually have a greater number of intersection points. In some embodiments, the number of trios tested is reduced by setting a criterion value U equal to the greatest number of intersection points in any intersection region. For example, only regions or combinations of regions having a number of intersection points exceeding the criteria number U are checked. If there are no solutions, U may be reset to U−1 and the process may be repeated. For example, by setting U=6, there are only five regions, $\rho_{1,1,1}$, $\rho_{2,2,2}$, $\rho_{3,3,3}$, $\rho_{1,2,3}$, $\rho_{3,2,1}$, having six intersection points need to be checked. The region subscripts may be presented as a single number vector, e.g., $\rho_{1,1,1}=[1\ 1\ 1]$; and the combination of $\rho_{3,2,1}$, $\rho_{1,1,1}$, and $\rho_{2,2,2}$ may be written as a matrix, e.g., $$\begin{bmatrix} 3 & 2 & 1 \\ 1 & 1 & 1 \\ 2 & 2 & 2 \end{bmatrix}.$$

There are nine additional combinations exist in FIG. 22:

$$\begin{bmatrix} 3 & 2 & 1 \\ 1 & 1 & 1 \\ 3 & 3 & 3 \end{bmatrix}, \begin{bmatrix} 3 & 2 & 1 \\ 1 & 1 & 1 \\ 1 & 2 & 3 \end{bmatrix}, \begin{bmatrix} 3 & 2 & 1 \\ 2 & 2 & 2 \\ 3 & 3 & 3 \end{bmatrix}, \begin{bmatrix} 3 & 2 & 1 \\ 2 & 2 & 2 \\ 1 & 2 & 3 \end{bmatrix}, \begin{bmatrix} 3 & 2 & 1 \\ 3 & 3 & 3 \\ 1 & 2 & 3 \end{bmatrix},$$

$$\begin{bmatrix} 1 & 1 & 1 \\ 2 & 2 & 2 \\ 3 & 3 & 3 \end{bmatrix}, \begin{bmatrix} 1 & 1 & 1 \\ 2 & 2 & 2 \\ 1 & 2 & 3 \end{bmatrix}, \begin{bmatrix} 1 & 1 & 1 \\ 3 & 3 & 3 \\ 1 & 2 & 3 \end{bmatrix}, \begin{bmatrix} 2 & 2 & 2 \\ 3 & 3 & 3 \\ 1 & 2 & 3 \end{bmatrix}.$$

Because the minimal solution alone can generate all of the shadows in the scene, each column of the minimal solution matrix has the numbers 1, 2, 3 (in no particular order). Accordingly, the 6th combination above having $\rho_{1,1,1}$, $\rho_{2,2,2}$, and $\rho_{3,3,3}$ is the minimal solution. This approach finds the minimal solution by determining whether there is at least one intersection region in every shadow region. This approach, however, may be time-consuming upon reducing U to 3, as the regions that have three intersection point require a more complicated check. In some embodiments, the three-point regions are neglected since they are almost never a part of a minimal solution.

In some embodiments, the 3D scenes are decomposed into a number of 2D scenes that can be quickly solved by the approaches as described above to determine the 3D shape of the objects. Because many of these 2D scenes share the same properties (e.g., the shape or location of the intersection regions), the solution of one 2D slice may be used to determine the solution of the next 2D slice; this may improve the computational efficiency.

The light sources may be positioned to lie in a plane. In one embodiment, a number of "bar" light sources are combined with "point" light sources to accomplish more complex lighting arrangements. In another embodiment, multiple light arrays lying in a plane are combined with multiple outlier-resistant least squares fits to effectively reduce the computational complexity by incorporating previously known geometric parameters of the target object.

Figure 23:
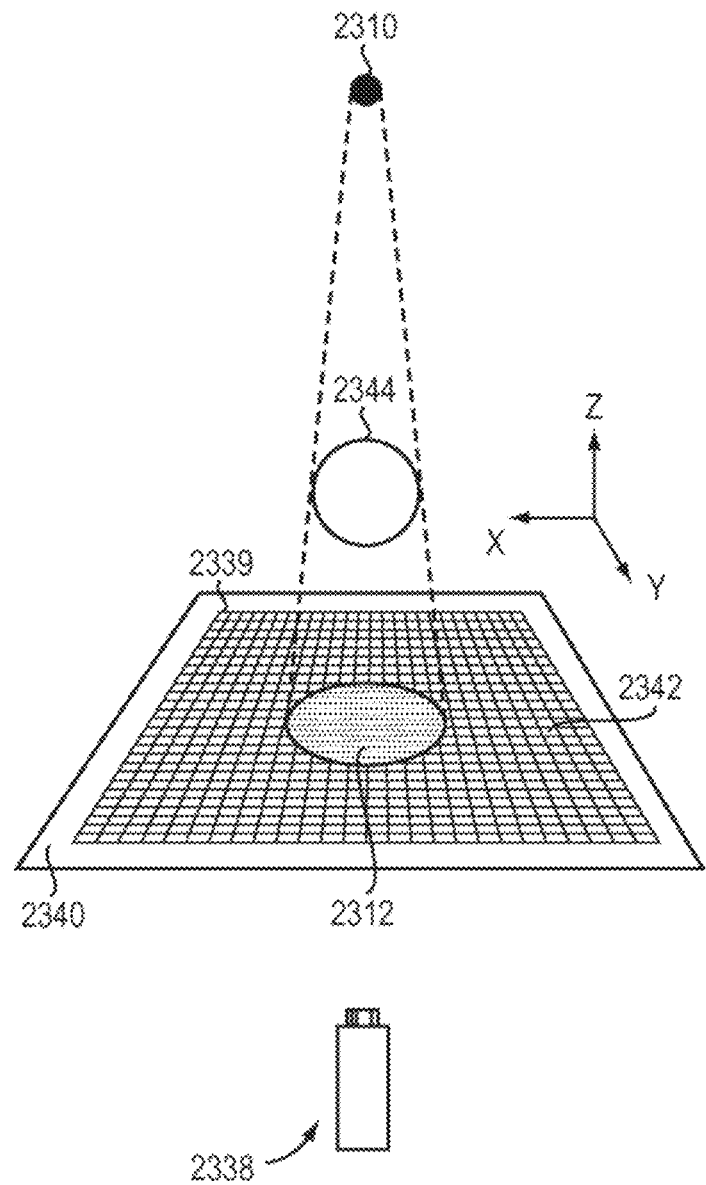
FIG. 23 illustrates an image coordinate system incorporated to define the locations of the shadows in accordance with an embodiment of the invention.

Referring to FIG. 23, in some embodiments, a shadow 2312 is cast on a translucent or imaginary surface 2340 such that the shadow 2312 can be viewed and captured by a camera 2338. The camera 2338 may take pictures with a number of light sensors (not shown in FIG. 23) arranged in a rectangular grid. In the camera 2338, there may be three such grids interlaced at small distances that essentially lie directly on top of each other. Each grid has a different color filter on all of its light sensors (e.g., red, green, or blue). Together, these sensors output three images, each comprising A×B light brightness values in the form of a matrix of pixels. The three color images together form an A×B×3 RGB image matrix. The image matrices may have their own coordinate system, which is defined by the set of matrix cell subscripts for a given pixel. For example, indices (x, y, z)=(0,0,0) may be defined and start in an upper left corner 2339 of the image. In one embodiment, the matrix of z=1 represents the red color image and z=2 and z=3 are the green and blue images, respectively. In one implementation, an "image row" is defined as all pixel values for a given constant coordinate value of y and an "image column" is defined as all pixel values for a given constant coordinate value of x.

Figure 24A:
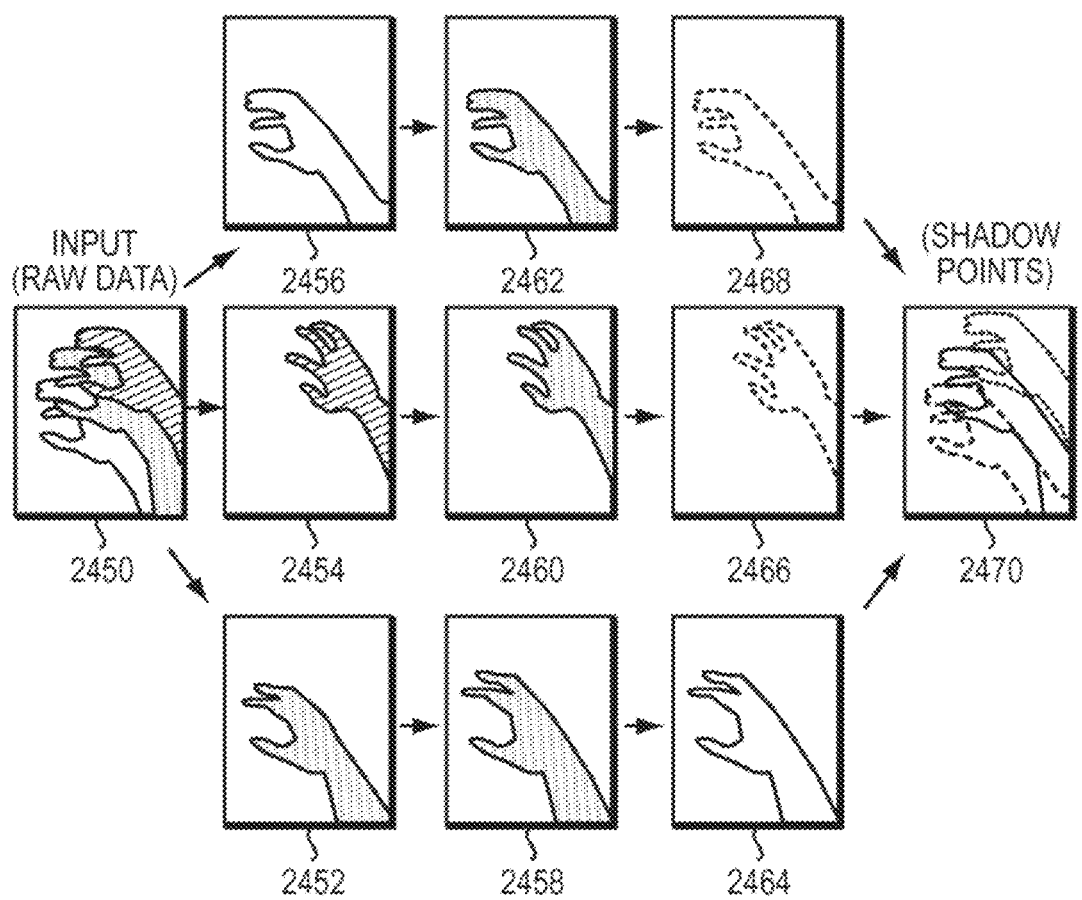
FIG. 24A illustrates separate color images captured using color filters in accordance with an embodiment of the invention.
Figure 24B:
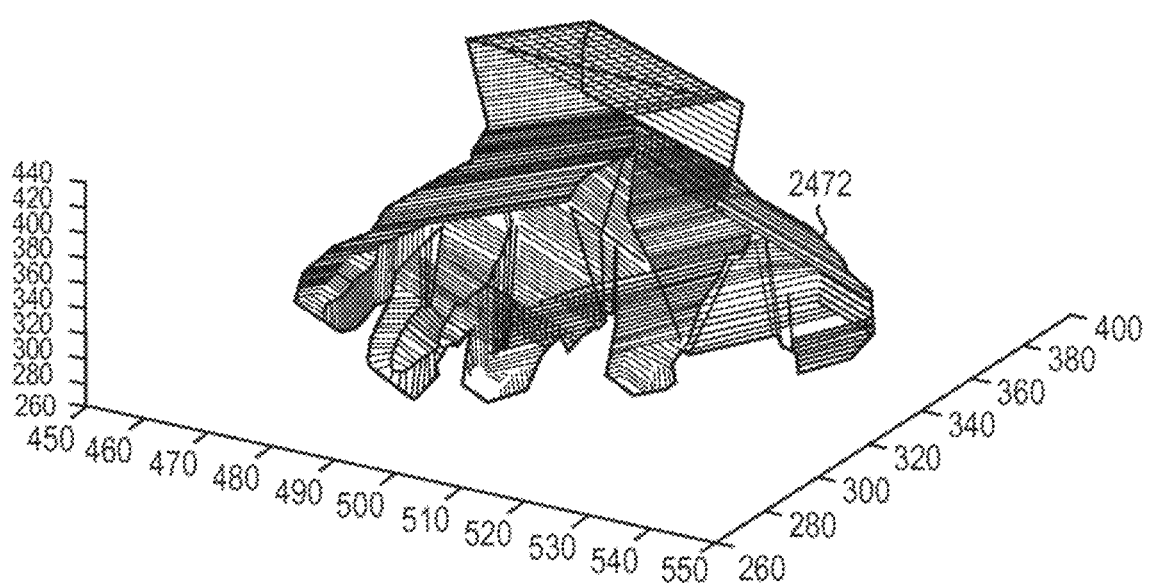
FIG. 24B depicts a reconstructed 3D image of the object.

Referring to FIG. 24A, a color image 2450 is split into images 2452, 2454, 2456 of three primary colors (i.e., red, green, and blue, respectively) by decomposing an A×B×3 full color matrix in a memory into 3 different A×B matrices, one for each z value between 1 and 3. Pixels in each image 2452, 2454, 2456 are then compared to a brightness threshold value to determine which pixels represent shadow and which represent background to thereby generate three shadow images 2458, 2460, 2462, respectively. The brightness threshold value may be determined by a number of statistical techniques. For example, in some embodiments, a mean pixel brightness is determined for each image and the threshold is set by subtracting three times the standard deviation of the brightness of the same pixels in the same image. Edges of the shadow images 2458, 2460, 2462 may then be determined to generate shadow point images 2464, 2466, 2468, respectively, using a conventional edge-determining technique. For example, the edge of each shadow image may be determined by subtracting the shadow image itself from an offset image created by offsetting a single pixel on the left (or right, top and/or bottom) side thereof. The 2D approaches described above may be applied to each of the shadow point images 2464, 2466, 2468 to determine the locations and colors of the objects. In some embodiments, shadow points in images 2464, 2466, 2468 are combined into a single A×B×3 color matrix or image 2470. Application of the 2D approaches described above to the combined shadow point image 2470 can then reconstruct an image of the object 2472 (e.g., a hand, as shown in FIG. 24B). Reconstructing an object (e.g., a hand) from shadows using various embodiments in the present invention may then be as simple as reconstructing a number of 2D ellipses. For example, fingers may be approximated by circles in 2D slices, and a palm may be approximated as an ellipse. This reconstruction is thereby converted into a practical number of simpler, more efficient reconstructions; the reconstructed 2D slices are then reassembled into the final 3D solution. These efficient reconstructions may be computed using a single processor or multiple processors operating in parallel to reduce the processing time.

In various embodiments, referring again to FIG. 23, the image coordinate system (i.e., the "imaging grid" 2342) is imposed on the surface 2340 to form a standard Cartesian coordinate system thereon such that the shadow 2312 can be easily defined. For example, each pixel (or light measurement value) in an image may be defined based on the coordinate integers x and y. In some embodiments, the camera 2338 is perpendicular to the surface 2340 on which shadows 2312 are cast and a point on a surface in the image grid is defined based on its coordinate inside an image taken by the camera 2338. In one embodiment, all light sources lie along a line or lines on a plane perpendicular to one of the axes to reduce the computational complexity. In various embodiments, the z axis of the coordinate system uses the same distance units and is perpendicular to the x and y axes of image grid 2342 to capture the 3D images of the shadows. For example, the light sources may be placed parallel to the x or y axis and perpendicular to the z-axis; a 3D captured shadow structure in the image coordinate system may be split into multiple 2D image slices, where each slice is a plane defined by a given row on the imaging grid and the line of light sources. The 2D slices may or may not share similar shapes. For example, the 2D intersection region of a 3D intersection region for a spherical object is very similar, i.e., a circle; whereas the 2D intersection region of a 3D intersection region for a cone shape varies across the positions of the 2D slices.

As described above, the shape of multiple objects may be discerned by determining a minimal solution of each 2D slice obtained from the 3D shadow. Since two slices next to each other are typically very similar, multiple slices often have the same minimal solution. In various embodiments, when two nearby slices have the same number of intersection regions, different combinations of the intersection regions are bypassed between the slices and the combination that works for a previous slice is reused on the next slice. If the old combination works for the new slice, this solution becomes a new minimal solution for the new slice and any further combinatorial checks are not performed. The reuse of old combinations thus greatly reduces computational time and complexity for complicated scenes. Although various embodiments described above are related to determining the shapes and positions of objects in 3D space using cross-sections obtained from the shadows cast by the objects, one of ordinary skill in the art will understand that cross-sections obtained utilizing different approaches, e.g., reflections from the objects, are within the scope of the current invention.

Figure 25A:
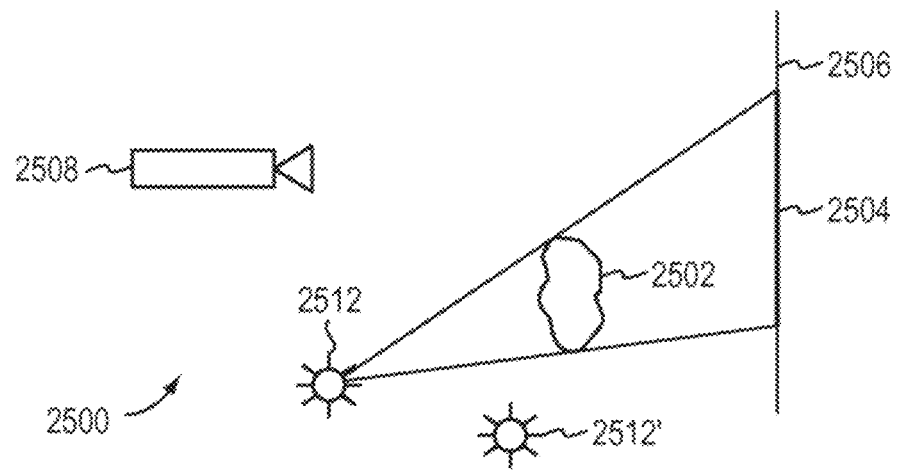
FIGS. 25A, 25B and 25C schematically illustrate a system for capturing an image of both the object and one or more shadows cast by the object from one or more light sources at known positions according to an embodiment of the present invention.
Figure 25B:
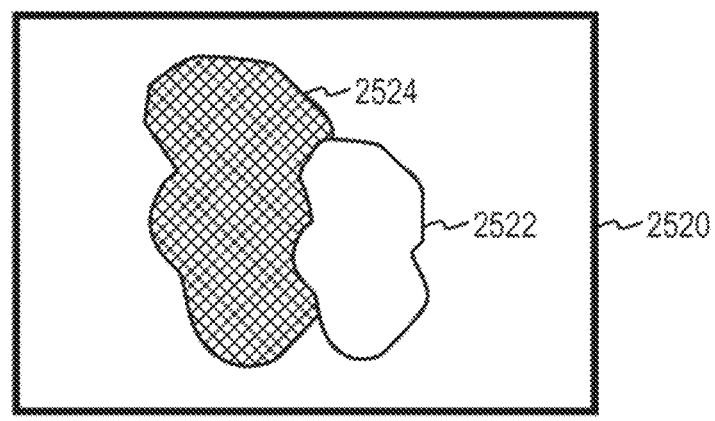

In still other embodiments, a single camera can be used to capture an image of both the object and one or more shadows cast by the object from one or more light sources at known positions. Such a system is illustrated in FIGS. 25A and 25B. FIG. 25A illustrates a system 2500 for capturing a single image of an object 2502 and its shadow 2504 on a surface 2506 according to an embodiment of the present invention. System 2500 includes a camera 2508 and a light source 2512 at a known position relative to camera 2508. Camera 2508 is positioned such that object of interest 2502 and surface 2506 are both within its field of view. Light source 2512 is positioned so that an object 2502 in the field of view of camera 2508 will cast a shadow onto surface 2506. FIG. 25B illustrates an image 2520 captured by camera 2508. Image 2520 includes an image 2522 of object 2502 and an image 2524 of shadow 2504. In some embodiments, in addition to creating shadow 2504, light source 2512 brightly illuminates object 2502. Thus, image 2520 will include brighter-than-average pixels 2522, which can be associated with illuminated object 2502, and darker-than-average pixels 2524, which can be associated with shadow 2504.

In some embodiments, part of the shadow edge may be occluded by the object. Where 30 the object can be reconstructed with fewer than four tangents (e.g., using circular cross-sections), such occlusion is not a problem. In some embodiments, occlusion can be minimized or eliminated by placing the light source so that the shadow is projected in a different direction and using a camera with a wide field of view to capture both the object and the unoccluded shadow. For example, in FIG. 25A, the light source could be placed at position 2512'.

Figure 25C:
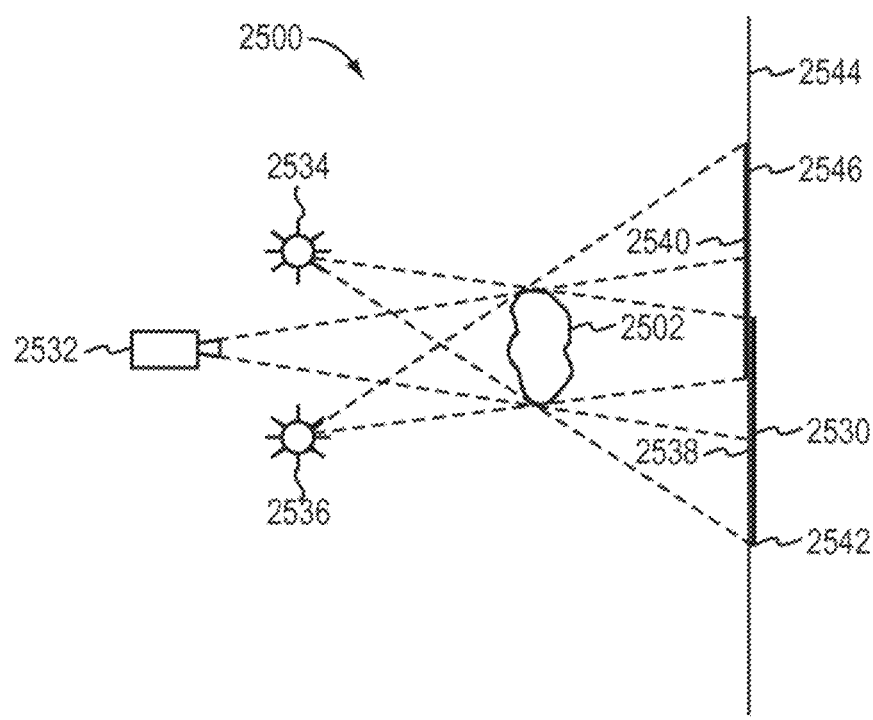

In other embodiments, multiple light sources can be used to provide additional visible edge points that can be used to define tangents. For example, FIG. 25C illustrates a system 2530 with a camera 2532 and two light sources 2534, 2536, one on either side of camera 2532. Light source 2534 casts a shadow 2538, and light source 2536 casts a shadow 2540. In an image captured by camera 2532, object 2502 may partially occlude each of shadows 2538 and 2540. However, edge 2542 of shadow 2538 and edge 2544 of shadow 2540 can both be detected, as can the edges of object 2502. These points provide four tangents to the object, two from the vantage point of camera 2532 and one each from the vantage point of light sources 2534 and 2536.

Figure 26:
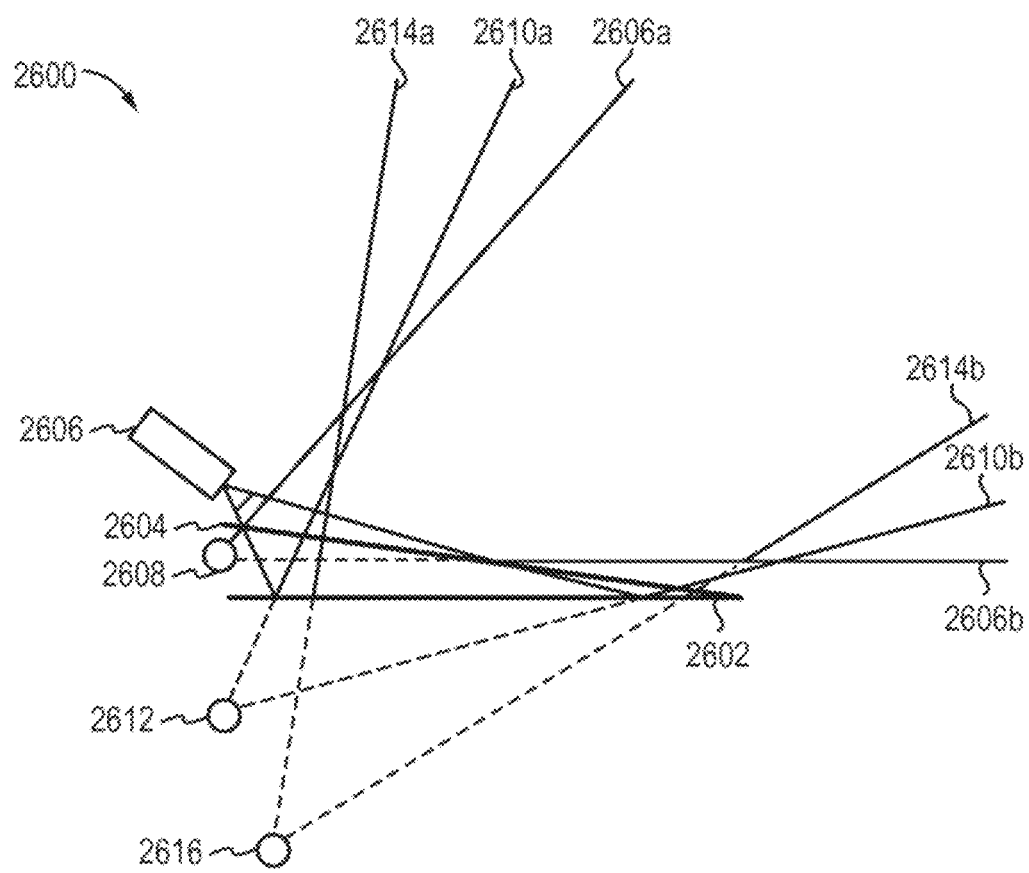
FIG. 26 schematically illustrates a camera-and-beamsplitter setup for a motion capture system according to another embodiment of the present invention.

As yet another example, multiple images of an object from different vantage points can be generated within an optical system, e.g., using beamsplitters and mirrors. FIG. 26 illustrates an image-capture setup 2600 for a motion capture system according to another embodiment of the present invention. A fully reflective front-surface mirror 2602 is provided as a "ground plane." A beamsplitter 2604 (e.g., a 50/50 or 70/30 beamsplitter) is placed in front of mirror 2602 at about a 20-degree angle to the ground plane. A camera 2606 is oriented toward beamsplitter 2604. Due to the multiple reflections from different light paths, the image captured by the camera can include ghost silhouettes of the object from multiple perspectives. This is illustrated using representative rays. Rays 2606a, 2606b indicate the field of view of a first virtual camera 2608; rays 2610a, 2610b indicate a second virtual camera 2612; and rays 2614a, 2614b indicate a third virtual camera 2616. Each virtual camera 2608, 2612, 2616 defines a vantage point for the purpose of projecting tangent lines to an object 2618.

Figure 27:
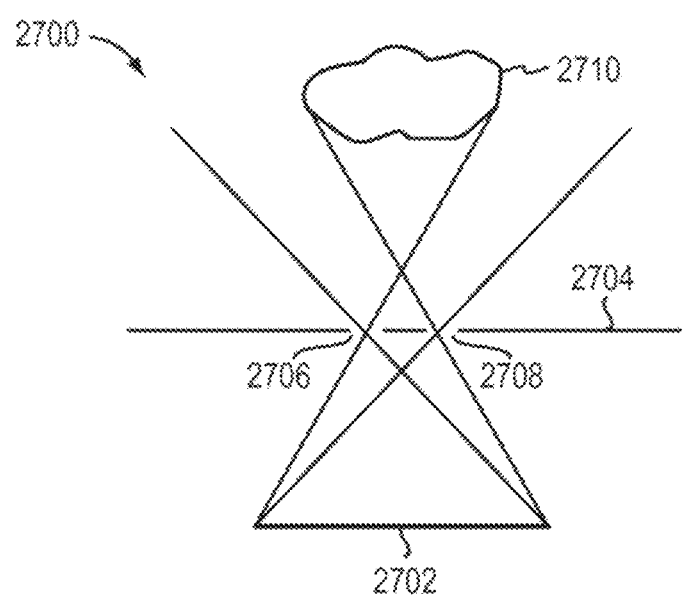
FIG. 27 schematically illustrates a camera-and-pinhole setup for a motion capture system according to another embodiment of the present invention.

Another embodiment uses a screen with pinholes arranged in front of a single camera. FIG. 27 illustrates an image capture setup 2700 using pinholes according to an embodiment of the present invention. A camera sensor 2702 is oriented toward an opaque screen 2704 in which are formed two pinholes 2706, 2708. An object of interest 2710 is located in the space on the opposite side of screen 2704 from camera sensor 2702. Pinholes 2706, 2708 can act as lenses, providing two effective vantage points for images of object 2710. A single camera sensor 2702 can capture images from both vantage points.

More generally, any number of images of the object and/or shadows cast by the object can be used to provide image data for analysis using techniques described herein, as long as different images or shadows can be ascribed to different (known) vantage points. Those skilled in the art will appreciate that any combination of cameras, beamsplitters, pinholes, and other optical devices can be used to capture images of an object and/or shadows cast by the object due to a light source at a known position.

Further, while the embodiments described above use light as the medium to detect edges of an object, other media can be used. For example, many objects cast a "sonic" shadow, either blocking or altering sound waves that impinge upon them. Such sonic shadows can also be used to locate edges of an object. (The sound waves need not be audible to humans; for example, ultrasound can be used.) The term "shadow" is herein used broadly to connote light or sonic shadows or other occlusion of a disturbance by an object, and the term "light" means electromagnetic radiation of any suitable wavelength(s) or wavelength range.

As described above, the general equation of an ellipse includes five parameters; where only four tangents are available, the ellipse is underdetermined, and the analysis proceeds by assuming a value for one of the five parameters. Which parameter is assumed is a matter of design choice, and the optimum choice may depend on the type of object being modeled. It has been found that in the case where the object is a human hand, assuming a value for the semimajor axis is effective. For other types of objects, other parameters may be preferred.

Further, while some embodiments described herein use ellipses to model the cross-sections, other shapes can be substituted. For instance, like an ellipse, a rectangle can be characterized by five parameters, and the techniques described above can be applied to generate rectangular cross-sections in some or all slices. More generally, any simple closed curve can be fit to a set of tangents in a slice. (The term "simple closed curve" is used in its mathematical sense throughout this disclosure and refers generally to a closed curve that does not intersect itself with no limitations implied as to other properties of the shape, such as the number of straight edge sections and/or vertices, which can be zero or more as desired.) The number of free parameters can be limited based on the number of available tangents. In another embodiment, a closed intersection region (a region fully bounded by tangent lines) can be used as the cross-section, without fitting a curve to the region. While this may be less accurate than ellipses or other curves, e.g., it can be useful in situations where high accuracy is not desired. For example, in the case of capturing motion of a hand, if the motion of the fingertips is of primary interest, cross-sections corresponding to the palm of the hand can be modeled as the intersection regions while fingers are modeled by fitting ellipses to the intersection regions.

In some embodiments, cross-slice correlations can be used to model all or part of the object using 3D surfaces, such as ellipsoids or other quadratic surfaces. For example, elliptical (or other) cross-sections from several adjacent slices can be used to define an ellipsoidal object that best fits the ellipses. Alternatively, ellipsoids or other surfaces can be determined directly from tangent lines in multiple slices from the same set of images. The general equation of an ellipsoid includes nine free parameters; using nine (or more) tangents from two or three (or more) slices, an ellipsoid can be fit to the tangents. Ellipsoids can be useful, e.g., for refining a model of fingertip (or thumb) position; the ellipsoid can roughly correspond to the last segment at the tip of a finger (or thumb). In other embodiments, each segment of a finger can be modeled as an ellipsoid. Other quadratic surfaces, such as hyperboloids or cylinders, can also be used to model an object or a portion thereof.

In some embodiments, an object can be reconstructed without tangent lines. For example, given a sufficiently sensitive time-of-flight camera, it would be possible to directly detect the difference in distances between various points on the near surface of a finger (or other curved object). In this case, a number of points on the surface (not limited to edge points) can be determined directly from the time-of-flight data, and an ellipse (or other shape) can be fit to the points within a particular image slice. Time-of-flight data can also be combined with tangent-line information to provide a more detailed model of an object's shape.

Any type of object can be the subject of motion capture using these techniques, and various aspects of the implementation can be optimized for a particular object. For example, the type and positions of cameras and/or light sources can be optimized based on the size of the object whose motion is to be captured and/or the space in which motion is to be captured. As described above, in some embodiments, an object type can be determined based on the 3D model, and the determined object type can be used to add type-based constraints in subsequent phases of the analysis. In other embodiments, the motion capture algorithm can be optimized for a particular type of object, and assumptions or constraints pertaining to that object type (e.g., constraints on the number and relative position of fingers and palm of a hand) can be built into the analysis algorithm. This can improve the quality of the reconstruction for objects of that type, although it may degrade performance if an unexpected object type is presented. Depending on implementation, this may be an acceptable design choice. For example, in a system for controlling a computer or other device based on recognition of hand gestures, there may not be value in accurately reconstructing the motion of any other type of object (e.g., if a cat walks through the field of view, it may be sufficient to determine that the moving object is not a hand).

Analysis techniques in accordance with embodiments of the present invention can be implemented as algorithms in any suitable computer language and executed on programmable processors. Alternatively, some or all of the algorithms can be implemented in fixed-function logic circuits, and such circuits can be designed and fabricated using conventional or other tools.

Computer programs incorporating various features of the present invention may be encoded on various computer readable storage media; suitable media include magnetic disk or tape, optical storage media such as compact disk (CD) or DVD (digital versatile disk), flash memory, and any other non-transitory medium capable of holding data in a computer-readable form. Computer readable storage media encoded with the program code may be packaged with a compatible device or provided separately from other devices. In addition program code may be encoded and transmitted via wired optical, and/or wireless networks conforming to a variety of protocols, including the Internet, thereby allowing distribution, e.g., via Internet download.

The motion capture methods and systems described herein can be used in a variety of applications. For example, the motion of a hand can be captured and used to control a computer system or video game console or other equipment based on recognizing gestures made by the hand. Full-body motion can be captured and used for similar purposes. In such embodiments, the analysis and reconstruction advantageously occurs in approximately real-time (e.g., times comparable to human reaction times), so that the user experiences a natural interaction with the equipment. In other applications, motion capture can be used for digital rendering that is not done in real time, e.g., for computer-animated movies or the like; in such cases, the analysis can take as long as desired. In intermediate cases, detected object shapes and motions can be mapped to a physical model whose complexity is suited to the application—i.e., which provides a desired processing speed given available computational resources. For example, the model may represent generic hands at a computationally tractable level of detail, or may incorporate the user's own hands by initial image capture thereof followed by texture mapping onto a generic hand model. The physical model is manipulated ("morphed") according to the detected object orientation and motion.

Thus, although the invention has been described with respect to specific embodiments, it will be appreciated that the invention is intended to cover all modifications and equivalents within the scope of the following claims.

Figure 28A:
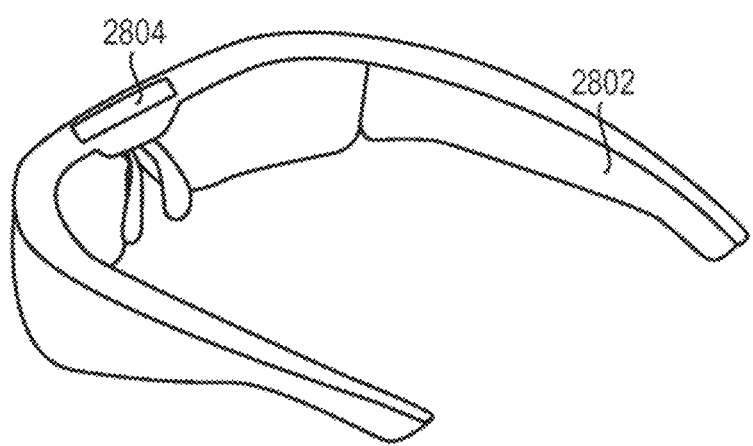
FIGS. 28A, 28B, and 28C depict a motion capture system operatively connected to a head-mounted device, a mobile device, and an authentication server, respectively.

In various embodiments, the system and method for capturing 3D motion of an object as described herein may be integrated with other applications, such as a head-mounted device or a mobile device. Referring to FIG. 28A, a head-mounted device 2802 typically includes an optical assembly that displays a surrounding environment or a virtual environment to the user; incorporation of the motion-capture system 2804 in the head-mounted device 2802 allows the user to interactively control the displayed environment. For example, the virtual environment may include virtual objects that can be manipulated by the user's hand gestures, which are tracked by the motion-capture system 2804. In one embodiment, the motion-capture system 2804 integrated with the head-mounted device 2802 detects a position and shape of user's hand and projects it on the display of the head-mounted device 2802 such that the user can see her gestures and interactively control the objects in the virtual environment. This may be applied in, for example, gaming or internet browsing.

Figure 28B:
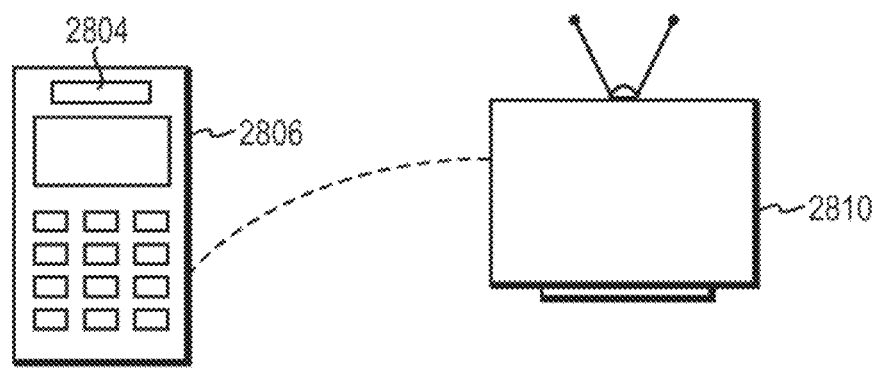

Referring to FIG. 28B, in some embodiments, the motion-capture system 2804 is employed in a mobile device 2806 that communicates with other devices 2810. For example, a television (TV) 2810 may include an input that connects to a receiver (e.g., a wireless receiver, a cable network or an antenna) to enable communication with the mobile device 2806. The mobile device 2806 first uses the embedded motion-capture system 2804 to detect movement of the user's hands, and to remotely control the TV 2810 based on the detected hand movement. For example, the user may perform a sliding hand gesture, in response to which the mobile device 2806 transmits a signal to the TV 2810; the signal may be a raw trajectory that circuitry associated with the TV interprets, or the mobile device 2806 may include programming that interprets the gesture and sends a signal (e.g., a code corresponding to "sliding hand") to the TV 2810. Either way, the TV 2810 responds by activating and displaying a control panel on the TV screen, and the user makes selections thereon using further gestures. The user may, for example, move his hand in an "up" or "down" direction, which the motion-capture system 2804 embedded in the mobile device 2806 converts to a signal that is transmitted to the TV 2810, and in response, the user's selection of a channel of interest from the control panel is accepted. Additionally, the TV 2810 may connect to a source of video games (e.g., video game console or web-based video game). The mobile device 2806 may capture the user's hand motion and transmit it to the TV for display thereon such that the user can remotely interact with the virtual objects in the video game.

Figure 28C:
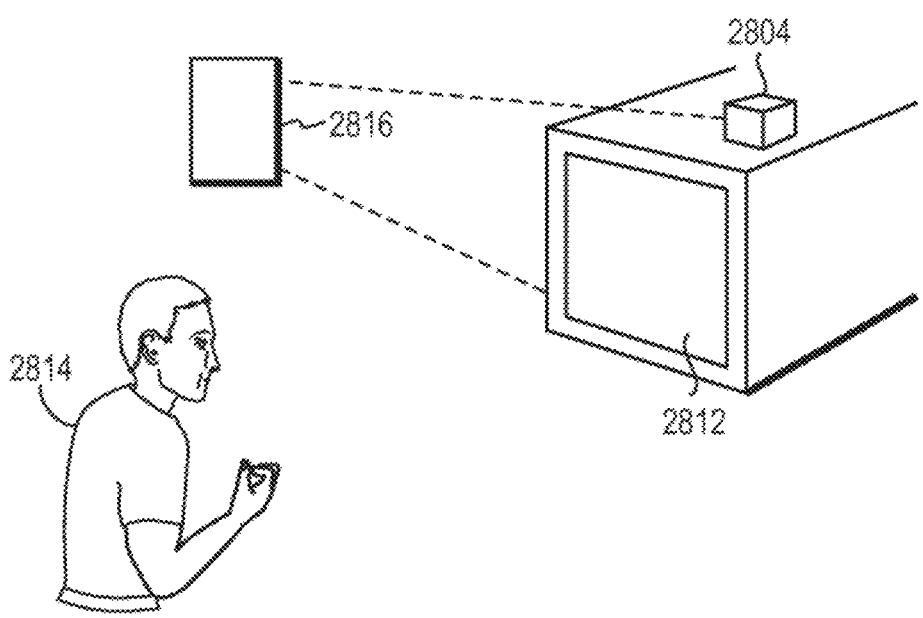

Referring to FIG. 28C, in various embodiments, the motion-capture system 2804 is integrated with a security system 2812. The security system 2812 may utilize the detected hand shape as well as hand jitter (detected as motion) in order to authenticate the user 2814. For example, an authentication server 2816 may maintain a database of users and corresponding hand shapes and jitter patterns. When a user 2814 seeks access to a secure resource 2812, the motion-capture system 2804 integrated with the resource 2812 (e.g., a computer) detects the user's hand shape and jitter pattern and then identifies the user 2814 by transmitting this data to the authentication server 2816, which compares the detected data with the database record corresponding to the access-seeking user 2814. If the user 2814 is authorized to access the secure resource 2812, the server 2816 transmits an acknowledgment to the resource 2812, which thereupon grants access. It should be stressed that the user 2814 may be authenticated to the secure system 2812 based on the shape of any part of a human body that may be detected and recognized using the motion-capture system 2804.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A system of recognizing gestures from a control object moving in three dimensional (3D) space, the system including:
one or more processors coupled to a memory, the memory loaded with computer instructions that, when executed by the one or more processors, implement actions including:
capturing images of a control object moving in 3D space using cameras having at least two geometrically distinct predetermined vantages;
calculating observed edges of the control object from the captured images;
fitting closed curves to the observed edges of the control object as captured in the images by selecting the closed curve from a family of similar closed curves that fit the observed edges of the control object as captured using an assumed parameter;
substituting one or more fitted parameters of a first fitted closed curve for one or more of the observed edges and the assumed parameter when fitting an adjacent second closed curve;
for a complex control object model that includes a palm and multiple fingers, applying the capturing images, calculating observed edges, fitting closed curves and substitute one or more fitted parameters actions to construct multiple fingers of control object appendages; and
fitting cross sections of a palm to observed edges of a palm as captured in the images;
repeatedly capturing, calculating, and fitting closed curves to the observed edges of the control object as the control object moves in the 3D space; and
analyzing differences in the positions of the fit closed curves to track motion of the control object while making a gesture in the 3D space; and
wherein results of the analyzing the gesture are interpreted as an instruction to some other program executing on a processor.

2. The system of claim 1, further configured to use a first fitted closed curve to filter fits of additional closed curves.

3. The system of claim 2, further including:
repeatedly applying the capturing images, calculating observed edges, fitting closed curves and use a first fitted closed curve to filter fits of additional closed curves actions of claim 2 over time; and
calculating motion of a complex control object over time based on differences between modeled locations of a complex control object over time.

4. The system of claim 1, further including:
repeatedly applying the capturing images, calculating observed edges, and fitting closed curves actions of claim 1 over time; and
calculating motion of the control object over time based on differences between modeled locations of the control object over time.

5. The system of claim 1, further configured to:
determining and fitting a circle selected from among the closed curves for a plurality of portions of the control object captured, including:
calculating three co planar tangents to observed edges of the control object from the captured images; and
fitting a circle to the control object using at least the three co planar tangents.

6. The system of claim 5, further including:
for a complex control object model that includes a palm and multiple fingers, applying the determining and fitting a circle actions of claim 5 to construct multiple fingers of control object appendages; and
fitting cross sections of a palm to observed edges of the palm as captured in the images.

7. The system of claim 6, further including:
repeatedly applying the determining and fitting a circle and fitting cross sections actions of claim 6 over time; and
calculating motion of a complex control object over time based on differences between modeled locations of the complex control object over time.

8. The system of claim 5, further including:
repeatedly applying the determining and fitting a circle actions of claim 5 over time; and
calculating motion of the control object over time based on differences between modeled locations of the control object over time.

9. A non-transitory computer readable medium storing a plurality of instructions for programming one or more processors to locate a control object appendage in three dimensional (3D) space, the instructions, when executed on the one or more processors, implementing actions including:
capturing images of a control object moving in 3D space using cameras having at least two geometrically distinct predetermined vantages;
calculating observed edges of the control object from the captured images;
fitting closed curves to the observed edges of the control object as captured in the images by selecting the closed curve from a family of similar closed curves that fit the observed edges of the control object as captured using an assumed parameter;

substituting one or more fitted parameters of a first fitted closed curve for one or more of the observed edges and the assumed parameter when fitting an adjacent second closed curve;

for a complex control object model that includes a palm and multiple fingers, applying the capturing images, calculating observed edges, fitting closed curves and substitute one or more fitted parameters actions to construct multiple fingers of control object appendages; and fitting cross sections of a palm to observed edges of a palm as captured in the images;

repeatedly capturing, calculating, and fitting closed curves to the observed edges of the control object as the control object moves in the 3D space; and analyzing differences in the positions of the fit closed curves to track motion of the control object while making a gesture in the 3D space; and wherein results of the analyzing the gesture are interpreted as an instruction to some other program executing on a processor.

10. The non-transitory computer readable medium of claim 9, further configured to use a first fitted closed curve to filter fits of additional closed curves to the contiguous cross-sections.

11. The non-transitory computer readable medium of claim 10, further including storing a plurality of instructions for programming one or more processors to locate a complex control object in 3D space, the instructions, when executed on the one or more processors, implementing actions including:

repeatedly applying the capturing images, calculating observed edges, fitting closed curves and use a first fitted closed curve to filter fits of additional closed curves actions of claim 10 over time; and calculating motion of a complex control object over time based on differences between modeled locations of a complex control object over time.

12. The non-transitory computer readable medium of claim 9, further including storing a plurality of instructions for programming one or more processors to track motion of a control object appendage in 3D space, the instructions, when executed on the one or more processors, implementing actions including:

repeatedly applying the capturing images, calculating observed edges, and fitting closed curves actions of claim 9 over time; and calculating motion of the control object over time based on differences between modeled locations of the control object over time.

13. The non-transitory computer readable medium of claim 9, further configured to:

determining and fitting a circle selected from among the closed curve for a plurality of portions of the control object captured, including:

calculating three co planar tangents to observed edges of the control object from the captured images; and fitting a circle to the control object using at least the three co planar tangents.

14. The non-transitory computer readable medium of claim 13, further including storing a plurality of instructions for programming one or more processors to locate a complex control object in 3D space, the instructions, when executed on the one or more processors, implementing actions including:

for a complex control object model that includes a palm and multiple fingers, applying the determining and fitting a circle actions of claim 13 to construct multiple fingers of control object appendages; and fitting cross sections of a palm to observed edges of the palm as captured in the images.

15. The non-transitory computer readable medium of claim 14, further including storing a plurality of instructions for programming one or more processors to track motion of a complex control object appendage in 3D space, the instructions, when executed on the one or more processors, implementing actions including:

repeatedly applying the determining and fitting a circle and fitting cross sections actions of claim 14 over time; and calculating motion of a complex control object over time based on differences between modeled locations of a complex control object over time.

16. The non-transitory computer readable medium of claim 13, further including storing a plurality of instructions for programming one or more processors to track motion of a control object appendage in 3D space, the instructions, when executed on the one or more processors, implementing actions including:

repeatedly applying the determining and fitting a circle actions of claim 13 over time; and calculating motion of the control object over time based on differences between modeled locations of the control object over time.

* * * * *